US010256415B2

(12) United States Patent
Sato et al.

(10) Patent No.: US 10,256,415 B2
(45) Date of Patent: Apr. 9, 2019

(54) LIGHT-EMITTING MATERIAL, ORGANIC LIGHT-EMITTING DEVICE, AND COMPOUND

(71) Applicant: KYULUX, INC., Fukuoka-shi, Fukuoka (JP)

(72) Inventors: Tadahisa Sato, Nagaoka (JP); Shun Unayama, Nagaoka (JP); Jie Li, Fukuoka (JP); Chihaya Adachi, Fukuoka (JP)

(73) Assignee: KYULUX, INC., Fukuoka-Shi, Fukuoka (JP)

( * ) Notice: Subject to any disclaimer, the term of this patent is extended or adjusted under 35 U.S.C. 154(b) by 124 days.

(21) Appl. No.: 15/129,070

(22) PCT Filed: Mar. 6, 2015

(86) PCT No.: PCT/JP2015/056623
§ 371 (c)(1),
(2) Date: Sep. 26, 2016

(87) PCT Pub. No.: WO2015/146541
PCT Pub. Date: Oct. 1, 2015

(65) Prior Publication Data
US 2017/0110670 A1    Apr. 20, 2017

(30) Foreign Application Priority Data

Mar. 27, 2014    (JP) .................. 2014-066316

(51) Int. Cl.
*H01L 51/00*    (2006.01)
*C07D 487/14*    (2006.01)
(Continued)

(52) U.S. Cl.
CPC ........ *H01L 51/0072* (2013.01); *C07D 487/04* (2013.01); *C07D 487/14* (2013.01);
(Continued)

(58) Field of Classification Search
CPC combination set(s) only.
See application file for complete search history.

(56) References Cited

U.S. PATENT DOCUMENTS

2009/0167167 A1* 7/2009 Aoyama .............. C07D 487/04
                                                                                313/504

FOREIGN PATENT DOCUMENTS

| CN | 101501037 A | 8/2009 |
|---|---|---|
| JP | 2006232793 A | 9/2006 |

(Continued)

OTHER PUBLICATIONS

International Search Opinion, Japanese International Preliminary Report on Patentability in Corresponding appl.PCT/JP2015/056623, dated Oct. 6, 2016.
(Continued)

*Primary Examiner* — Jennifer A Chriss
*Assistant Examiner* — Sean M DeGuire
(74) *Attorney, Agent, or Firm* — Browdy and Neimark, PLLC

(57) ABSTRACT

An organic light-emitting device having a compound represented by the following general formula in a light-emitting layer thereof has a high light emission efficiency. $R^1$ to $R^5$ each independently represent a hydrogen atom or a substituent having a Hammett $\sigma_p$ value of 0 or more. $R^6$ to $R^{20}$ each independently represent a hydrogen atom or a substituent, provided that at least one of $R^6$ to $R^{20}$ represents a substituted or unsubstituted N,N-diarylamino group. m represents 1 or 2.

(Continued)

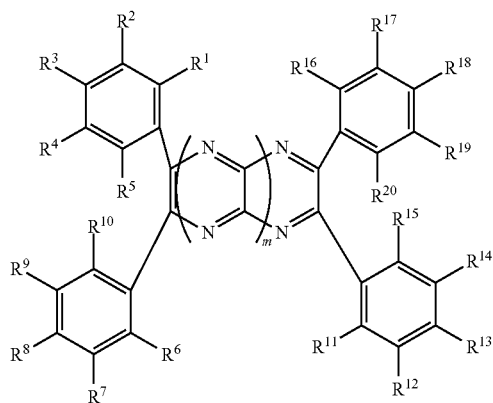

13 Claims, 6 Drawing Sheets

(51) Int. Cl.
C07D 487/04 (2006.01)
C09K 11/06 (2006.01)
H01L 51/50 (2006.01)
(52) U.S. Cl.
CPC .......... C09K 11/06 (2013.01); H01L 51/0059 (2013.01); H01L 51/0071 (2013.01); C09K 2211/1007 (2013.01); C09K 2211/1044 (2013.01); H01L 51/5012 (2013.01)

(56) References Cited

FOREIGN PATENT DOCUMENTS

| JP | 2007197426 A | 8/2007 |
| JP | 2010105927 A | 5/2010 |
| JP | 5227510 B2 | 7/2013 |
| JP | 2013134947 A | 7/2013 |
| JP | 2014009352 A | * 1/2014 |
| JP | 2014009352 A | 1/2014 |
| JP | 2014011437 A | 1/2014 |
| WO | 2007142216 A | 12/2007 |
| WO | 2012039561 A1 | 3/2012 |

OTHER PUBLICATIONS

International Search Report, in Corresponding appl.PCT/JP2015/056623, dated Jun. 9, 2015.
Rohman et al "One-Pot Synthesis of Unsymmetrical Benzils by Oxidative Coupling Using Selenium Diozide and p-Toluenesulfonic Acid Monohydrate" European Journal of Organic Chemistry.320-328 (2012).
Ono et al "Synthesis and Electroluminescence Properties of fac-Tris (2-phenylpyridine)-iridium Derivatives Containing-Hole-Trapping Moieties" European Journal of Organic Chemistry. 3676-3683 (2006).
Hicks et al "Analysis of the inhibition of mammalian carboxylesterases by novel fluorobenzoins and fluorobenzils" Bioorganic & Medicinal Chemistry. 15 : 3801-3817 (2007).
Chinese Office Action dated Jun. 7, 2017 issued in the corresponding Chinese patent application No. 201580016425.4 with its English Machine Translation.

* cited by examiner

LIGHT-EMITTING MATERIAL, ORGANIC LIGHT-EMITTING DEVICE, AND COMPOUND

TECHNICAL FIELD

The present invention relates to an organic light-emitting device having a high light emission efficiency. The invention also relates to a light-emitting material and a compound that can be effectively used for the organic light-emitting device.

BACKGROUND ART

An organic light-emitting device, such as an organic electroluminescent device (organic EL device), has been actively studied for enhancing the light emission efficiency thereof. In particular, various studies for enhancing the light-emitting efficiency have been made by newly developing and combining a light-emitting material, a host material, an electron transporting material, a hole transporting material and the like constituting an organic electroluminescent device. There are studies relating to an organic electroluminescent device utilizing a compound having a structure containing a pyrazine ring having an (N, N-diarylamino) aryl group substituted thereon.

For example, Patent Document 1 describes the use of the polyazaacene compound represented by the following general formula as a light-emitting material of an organic light-emitting device. The literature states that in the general formula, $R^1$ to $R^4$ each represent a hydrogen atom or a substituted or unsubstituted (N, N-diarylamino) aryl group, provided that at least one of $R^1$ to $R^4$ represents a substituted or unsubstituted (N,N-diarylamino)aryl group, and $W^1$, $W^2$, $X^1$, $X^2$, $Y^1$, $Y^2$, $Z^1$, and $Z^2$ each represent a carbon atom or a nitrogen atom. However, Patent Document 1 does not describe the compound, in which $R^1$ to $R^4$ each are a substituent other than an (N,N-diarylamino) aryl group.

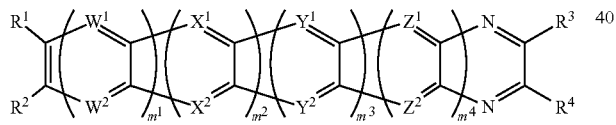

Patent Document 2 describes the use of the pyrazine derivative represented by the following general formula (g-1) as a host material and a light-emitting material of a light-emitting layer constituting a light-emitting device. The literature states that in the general formula, $R^1$ to $R^3$ each represent any one of a hydrogen atom, an alkyl group, or an aryl group, A represents any of substituents represented by the general formulae (a-1) to (a-4), $R^4$ represents an alkyl group or an aryl group, $R^5$ to $R^7$ each represent any of a hydrogen atom, an alkyl group, and an aryl group, $Ar^1$ to $Ar^7$ each represent an aryl group, and a represents an arylene group. The literature describes as specific examples an example using the pyrazine derivative, in which A is an N,N-diphenylamino group, $R^3$ is a 4-(N,N-diphenylamino) phenyl group, and $R^1$ and $R^2$ each are a phenyl group, as a host material for a phosphorescent material. However, all the compounds described in Patent Document 2 are pyrazine derivatives having a monocyclic pyrazine ring as the core structure, and the literature does not describe a compound having a structure containing plural pyrazine rings fused to each other (i.e., a polyazaacene structure) as the core structure.

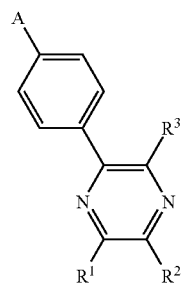

(g-1)

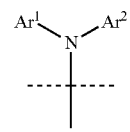

(a-1)

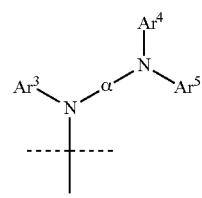

(a-2)

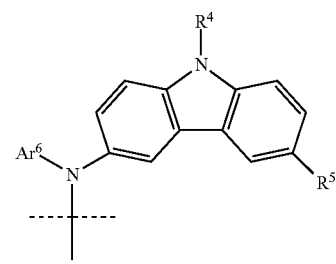

(a-3)

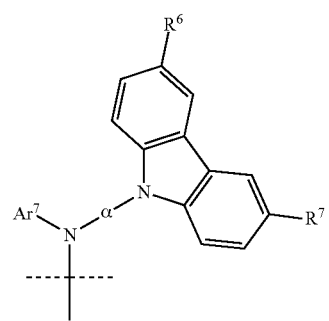

(a-4)

CITATION LIST

Patent Literatures

Patent Document 1: JP-A-2014-9352
Patent Document 2: Japanese Patent No. 5,227,510

SUMMARY OF INVENTION

Technical Problem

As described above, Patent Document 1 describes that the polyazaacene compound having an (N,N-diarylamino) aryl group substituted thereon is capable of being used as a light-emitting material. However, in all the compounds described in Patent Document 1, the substituent substituted on a polyazaacene structure is an (N,N-diarylamino) aryl group, and the literature does not describe a compound having a polyazaacene structure having other substituents substituted thereon.

In view of this, the present inventors have started various investigations on a group of compounds having a structure containing a polyazaacene structure having an (N,N-diarylamino)aryl group substituted thereon, and the inventors have firstly found that a group of compounds having a structure containing a polyazaacene structure having an (N,N-diarylamino)aryl group and an aryl group having no N,N-diarylamino group substituted thereon has high usefulness as a light-emitting material, and have decided to continue further investigations. As described above, Patent Document 1 describes the usefulness as a light-emitting material of an organic light-emitting device of the compound having a polyazaacene structure having an (N,N-diarylamino) aryl group substituted thereon. However, the literature does not investigate a compound containing a polyazaacene structure having an (N, N-diarylamino) aryl group and an aryl group having no N,N-diarylamino group substituted thereon. On the other hand, Patent Document 2 describes a compound containing a monocyclic pyrazine ring having a 4-(N,N-diarylamino)phenyl group and a phenyl group having no substituent substituted thereon. However, the literature does not describe a compound having a polyazaacene structure containing plural pyrazine rings fused to each other. Accordingly, the usefulness of a compound containing a polyazaacene structure having an (N,N-diarylamino)aryl group and an aryl group having no N,N-diarylamino group substituted thereon as a light-emitting material cannot be expected.

Under the circumstances, the inventors have investigated for an object of evaluating the usefulness as a light-emitting material of an organic light-emitting device of a polyazaacene compound having an (N,N-diarylamino) aryl group and an aryl group having no N,N-diarylamino group substituted thereon. Furthermore, the inventors have made earnest investigations for an object of providing a general formula of the compounds useful as a light-emitting material and generalizing the structure of an organic light-emitting material having a high light emission efficiency.

Solution to Problem

As a result of the earnest investigations for achieving the objects, the inventors have clarified that a polyazaacene compound having a particular structure is significantly useful as a light-emitting material of an organic light-emitting device. The inventors also have found that the polyazaacene compounds include a compound that is useful as a delayed fluorescent emitter, and have clarified that an organic light-emitting device having a high light emission efficiency can be provided. Based on the knowledge, the inventors have provided the following inventions as measures for achieving the objects.

[1] A light-emitting material containing a compound represented by the following general formula (1):

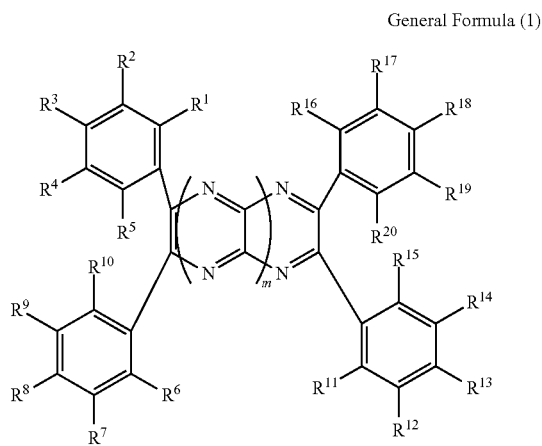

General Formula (1)

wherein in the general formula (1), $R^1$ to $R^5$ each independently represent a hydrogen atom or a substituent having a Hammett $\sigma_p$ value of 0 or more; $R^6$ to $R^{20}$ each independently represent a hydrogen atom or a substituent, provided that at least one of $R^6$ to $R^{20}$ represents a substituted or unsubstituted N,N-diarylamino group; and m represents 1 or 2.

[2] The light-emitting material according to the item [1], wherein the substituent having a Hammett $\sigma_p$ value of 0 or more is a halogen atom, an acyloxy group, an alkoxycarbonyl group, an aryloxycarbonyl group, a phenyl group, or a cyano group.

[3] The light-emitting material according to the item [1] or [2], wherein the substituted or unsubstituted N,N-diarylamino group is a group represented by the following general formula (2):

General Formula (2)

wherein in the general formula (2), $A^1$ and $Ar^2$ each independently represent a substituted or unsubstituted aromatic group having from 6 to 10 carbon atoms; and * represents a bonding position, provided that in the case where the compound represented by the general formula (1) has plural groups each represented by the general formula (2), the groups represented by $Ar^1$ may be the same as or different from each other, and the groups represented by $Ar^2$ may be the same as or different from each other.

[4] The light-emitting material according to the item [3], wherein $Ar^1$ and $Ar^2$ are bonded directly or indirectly to each other to form a ring.

[5] The light-emitting material according to the item [4], wherein the group represented by the general formula (2) is represented by the following general formula (3):

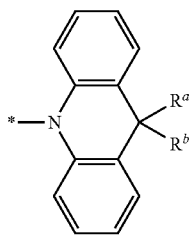

General Formula (3)

wherein in the general formula (3), $R^a$ and $R^b$ each independently represent a hydrogen atom, a substituted or unsubstituted alkyl group having from 1 to 5 carbon atoms, or a substituted or unsubstituted aromatic group having from 6 to 10 carbon atoms; and * represents a bonding position, provided that in the case where the compound represented by the general formula (1) has plural groups each represented by the general formula (3), the groups represented by Ra may be the same as or different from each other, and the groups represented by Rb may be the same as or different from each other.

[6] The light-emitting material according to any one of the items [1] to [5], wherein in the general formula (1), m is 1.

[7] The light-emitting material according to any one of the items [1] to [6], wherein the light-emitting material emits delayed fluorescent light.

[8] A compound represented by the following general formula (11):

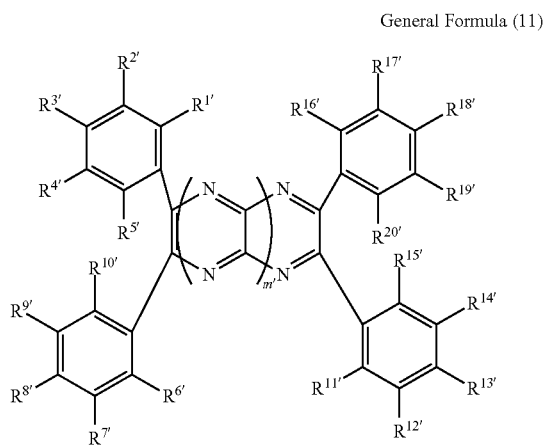

General Formula (11)

wherein in the general formula (11), $R^{1'}$ to $R^{5'}$ each independently represent a hydrogen atom or a substituent having a Hammett $\sigma_p$ value of 0 or more; $R^{6'}$ to $R^{20'}$ each independently represent a hydrogen atom or a substituent, provided that at least one of $R^{6'}$ to $R^{20'}$ represents a substituted or unsubstituted N,N-diarylamino group; and m' represents 1 or 2.

[9] The compound according to the item [8], wherein the compound represented by the general formula (11) is represented by the following general formula (12):

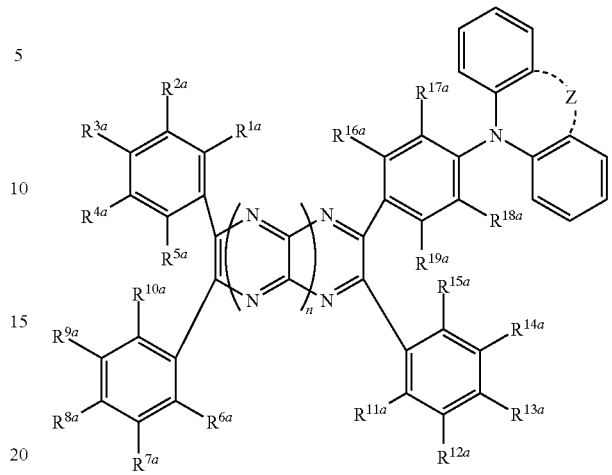

General Formula (12)

wherein in the general formula (12), $R^{1a}$ to $R^{5a}$ and $R^{16a}$ to $R^{19a}$ each independently represent a hydrogen atom or a substituent having a Hammett $\sigma_p$ value of 0 or more; $R^{6a}$ to $R^{15a}$ each independently represent a hydrogen atom, a substituent having a Hammett $\sigma_p$ value of 0 or more, or a substituted or unsubstituted N,N-diarylamino group; n represents 1 or 2; and Z represents a linking group containing a carbon chain for forming a 6-membered or 7-membered ring, or an oxygen atom for forming a 6-membered ring.

[10] The compound according to the item [9], wherein $R^{1a}$ to $R^{5a}$ each independently represent a hydrogen atom or a fluorine atom.

[11] An organic light-emitting device containing a substrate having thereon a light-emitting layer containing the light-emitting material according to any one of the items [1] to [7].

[12] The organic light-emitting device according to the item [11], wherein the light-emitting device emits delayed fluorescent light.

[13] The organic light-emitting device according to the item [11] or [12], wherein the light-emitting device is an organic electroluminescent device.

Advantageous Effects of Invention

The organic light-emitting device of the invention has a feature of having a high light emission efficiency. The compound and the light-emitting material of the invention that are utilized in a light-emitting layer of an organic light-emitting device have a feature of being capable of enhancing the light emission efficiency thereof. The use of the compound and the light-emitting material of the invention that emit delayed fluorescent light can drastically increase the light emission efficiency.

DESCRIPTION OF EMBODIMENTS

Figure 1:
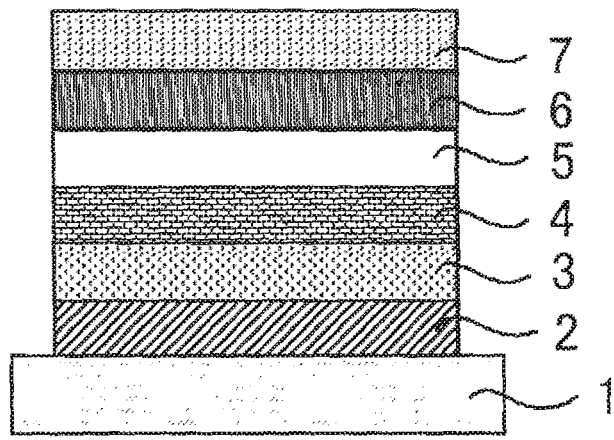
FIG. 1 is a schematic cross sectional view showing an example of a layer structure of an organic electroluminescent device.

The contents of the invention will be described in detail below. The constitutional elements may be described below with reference to representative embodiments and specific examples of the invention, but, the invention is not limited to the embodiments and the examples. In the description, a numerical range expressed with reference to an upper limit and/or a lower limit means a range that includes the upper limit and/or the lower limit. In the invention, the hydrogen atom in the molecule that is present in the compound used in the invention is not particularly limited in isotope species, and for example, all the hydrogen atoms in the molecule may be $^1$H, and all or a part of them may be $^2$H (deuterium (D)).

Compound Represented by General Formula (1)

The light-emitting material of the invention contains a compound represented by the following general formula (1)

General Formula (1)

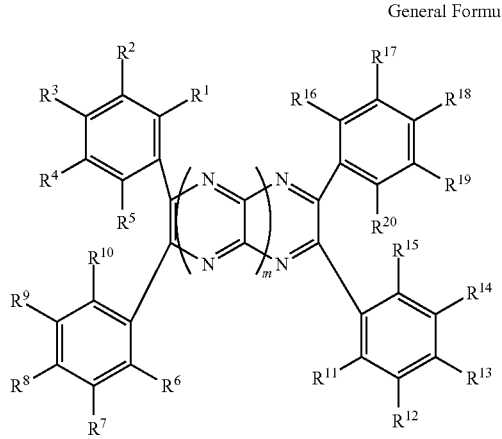

In the general formula (1), $R^1$ to $R^5$ each independently represent a hydrogen atom or a substituent having a Hammett $\sigma_p$ value of 0 or more. The Hammett $\sigma_p$ value is a value that is calculated by the following expression (I). The $\sigma_p$ value that is 0 or more means that the substituent is an electron withdrawing substituent:

$$\sigma_p = \log K_X - \log K_H \qquad \text{Expression (I)}$$

wherein in the expression (I), $K_H$ represents an ionization constant of benzoic acid in water at 25° C., and $K_X$ represents an ionization constant of benzoic acid having a substituent at the p-position thereof in water at 25° C.

Examples of the substituent having a Hammett $\sigma_p$ value of 0 or more include a halogen atom, an acyloxy group, an alkoxycarbonyl group, an aryloxycarbonyl group, a phenyl group, and a cyano group, and among these, a halogen atom and a cyano group are preferred, and a halogen atom is more preferred. The number of the substituent in $R^1$ to $R^5$ is not particularly limited, and all thereof may be unsubstituted (i.e., hydrogen atoms). In the case where two or more of $R^1$ to $R^5$ each represent the substituent, the plural substituents may be the same as or different from each other.

$R^6$ to $R^{20}$ each independently represent a hydrogen atom or a substituent, provided that at least one of $R^6$ to $R^{20}$ represents a substituted or unsubstituted N,N-diarylamino group. The number of a substituted or unsubstituted N,N-diarylamino group represented by $R^6$ to $R^{20}$ is not particularly limited, as far as the number is 1 or more, and the upper limit of the number of the substituted or unsubstituted N,N-diarylamino group in each of $R^6$ to $R^{10}$, $R^{11}$ to $R^{15}$, and $R^{16}$ to $R^{20}$ is preferably 2, and more preferably 1. $R^6$ to $R^{20}$ that represent a substituted or unsubstituted N,N-diarylamino group are not particularly limited, and are preferably from 1 to 3 of $R^7$ to $R^9$, $R^{12}$ to $R^{14}$, and $R^{17}$ to $R^{19}$, more preferably from 1 to 3 of $R^7$, $R^8$, $R^{12}$, $R^{13}$, $R^{17}$, and $R^{18}$, further preferably from 1 to 3 of $R^8$, $R^{13}$, and $R^{18}$, and particularly preferably at least one of $R^{13}$ and $R^{18}$.

The substituted or unsubstituted N,N-diarylamino group that may be represented by $R^6$ to $R^{20}$ is preferably a group represented by the following general formula (2).

General Formula (2)

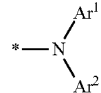

In the general formula (2), * represents a bonding position, and $Ar^1$ and $Ar^2$ each independently represent a substituted or unsubstituted aromatic group having from 6 to carbon atoms. The aromatic group referred herein may be one formed of a monocyclic ring or one containing a fused ring. Preferred examples thereof include a phenyl group and a naphthyl group, and a phenyl group is more preferred. Specific examples thereof include a phenyl group, a 1-naphthyl group, and a 2-naphthyl group. $Ar^1$ and $Ar^2$ may be the same as or different from each other. In the case where the plural substituted or unsubstituted N,N-diarylamino groups each represented by the general formula (2) are present in the molecule, the groups represented by $Ar^1$ in the plural substituted or unsubstituted N,N-diarylamino groups may be the same as or different from each other, and the groups represented by $Ar^2$ in the plural substituted or unsubstituted N,N-diarylamino groups may be the same as or different from each other.

In the general formula (2), $Ar^1$ and $Ar^2$ may be bonded to each other to form a cyclic structure. In the case where $Ar^1$ and $Ar^2$ are bonded to each other to form a cyclic structure, $Ar^1$ and $Ar^2$ may be bonded directly or indirectly to each other to form a ring. Specifically, the aromatic group constituting $Ar^1$ and the aromatic group constituting $Ar^2$ may be bonded to each other through a single bond, or may be bonded each other through a linking group. In the case where the aromatic groups are bonded to each other through a linking group, the linking group preferably has from 1 to 3 linking atoms, and more preferably 1 or 2 linking atoms. In the case where the number of the linking atoms is 2 or more, the linking atoms may have or may not have an unsaturated bond therebetween, and preferably have an unsaturated bond. Preferred examples of the linking group include a linking group represented by the following formula (4). In the formula (4), $R^{21}$ and $R^{22}$ each independently represent a hydrogen atom or a substituent, and $R^{21}$ and $R^{22}$ may be bonded to each other to form a cyclic structure. Examples of the cyclic structure include an aryl ring, such as a benzene ring and a naphthalene ring, a heteroaryl ring, such as a pyridine ring and a pyrazine ring, and an unsaturated aliphatic ring, such as a cyclopentadiene ring and a cyclohexene ring.

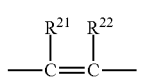

General Formula (4)

Specific examples of the N,N-diarylamino group represented by the general formula (2) include an N,N-diphenylamino group, an N-phenyl-N-(1-naphthyl)amino group, an N-phenyl-N-(2-naphthyl)amino group, an N,N-di(1-naphthyl)amino group, an N,N-di(2-naphthyl)amino group, a carbazol-9-yl group, and a 5H-dibenzo[b,f]azepin-5-yl group. Among these, an N, N-diphenylamino group, an N-phenyl-N-(1-naphthyl)amino group, a carbazol-9-yl group, and a 5H-dibenzo[b,f]azepin-5-yl group are preferred. The N,N-diarylamino groups exemplified herein may be further substituted.

The N,N-diarylamino group represented by the general formula (2) is also preferably a group represented by the following general formula (3)

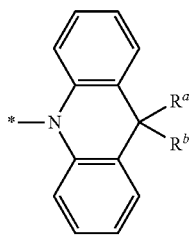

General Formula (3)

In the general formula (3), * represents a bonding position, and $R^a$ and $R^b$ each independently represent a hydrogen atom, a substituted or unsubstituted alkyl group having from 1 to 5 carbon atoms, or a substituted or unsubstituted aromatic group having from 6 to 10 carbon atoms. The alkyl group that may be represented by $R^a$ and $R^b$ is not particularly limited, as far as the alkyl group has from 1 to 5 carbon atoms, and is preferably a methyl group. For the descriptions and the preferred ranges of the aromatic group that may be represented by $R^a$ and $R^b$, reference may be made to the description and the preferred ranges of the aromatic group that may be represented by $Ar^1$ and $Ar^2$. $R^a$ and $R^b$ may be the same as or different from each other. In the case where the compound represented by the general formula (1) has plural groups each represented by the general formula (3), the groups represented by $R^a$ may be the same as or different from each other, and the groups represented by $R^b$ may be the same as or different from each other.

Examples of the substituent of the substituted aromatic group that may be represented by $Ar^1$ and $Ar^2$ in the general formula (2), the substituent of the substituted alkyl group and the substituted aromatic group that may be represented by $R^a$ and $R^b$ in the general formula (3), and substituent that may be represented by $R^{21}$ and $R^{22}$ in the general formula (4) include a hydroxyl group, a halogen atom, a cyano group, an alkyl group having from 1 to 20 carbon atoms, an alkoxy group having from 1 to 20 carbon atoms, a substituted or unsubstituted aryloxy group having from 6 to 40 carbon atoms, an alkylthio group having from 1 to 20 carbon atoms, an alkyl-substituted amino group having from 1 to 20 carbon atoms, an acyl group having from 2 to 20 carbon atoms, a heteroaryl group having from 3 to 40 carbon atoms, a diarylamino group having from 12 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, an alkoxy group having from 1 to 20 carbon atoms, a substituted or unsubstituted aryloxy group having from 6 to 40 carbon atoms, a substituted or unsubstituted heteroaryl group having from 3 to 40 carbon atoms, a substituted or unsubstituted diarylamino group having from 12 to 40 carbon atoms, and a substituted or unsubstituted carbazolyl group having from 12 to 40 carbon atoms. Further preferred examples of the substituent include a substituted or unsubstituted alkyl group having from 1 to 10 carbon atoms, a substituted or unsubstituted aryloxy group having from 6 to 40 carbon, atoms, and a substituted or unsubstituted diarylamino group having from 12 to 40 carbon atoms.

The alkyl group referred in the description herein may be any of linear, branched, and cyclic, and more preferably has from 1 to 6 carbon atoms, specific examples of which include a methyl group, an ethyl group, a propyl group, a butyl group, a tert-butyl group, a pentyl group, a hexyl group, and an isopropyl group. The alkoxy group may be any of linear, branched, and cyclic, and more preferably has from 1 to 6 carbon atoms, specific examples of which include a methoxy group, an ethoxy group, a propoxy group, a butoxy group, a tert-butoxy group, a pentyloxy group, a hexyloxy group, and an isopropoxy group. The two alkyl groups of the dialkylamino group may be the same as or different from each other, and are preferably the same as each other. The two alkyl groups of the dialkylamino group each may independently be any of linear, branched, and cyclic, and more preferably has from 1 to 6 carbon atoms, specific examples of which include a methyl group, an ethyl group, a propyl group, a butyl group, a pentyl group, a hexyl group, and an isopropyl group. The heteroaryl group may be formed only of a monocyclic ring or may contain a fused ring, specific examples of which include a pyridyl group, a pyridazyl group, a pyrimidyl group, a triazyl group, a triazolyl group, and a benzotriazolyl group. The heteroaryl group may be a group that is bonded through the hetero atom or a group that is bonded through the carbon atom constituting the heteroaryl group.

In the general formula (1), m represents 1 or 2, and preferably 1.

Specific examples of the compound represented by the general formula (1) are shown below. However, the compound represented by the general formula (1) capable of being used in the invention is not construed as being limited to the specific examples.

(1)

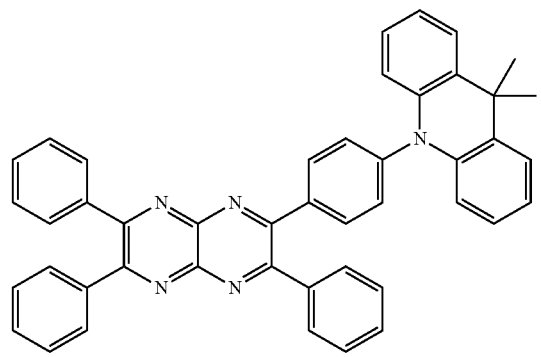

(2)

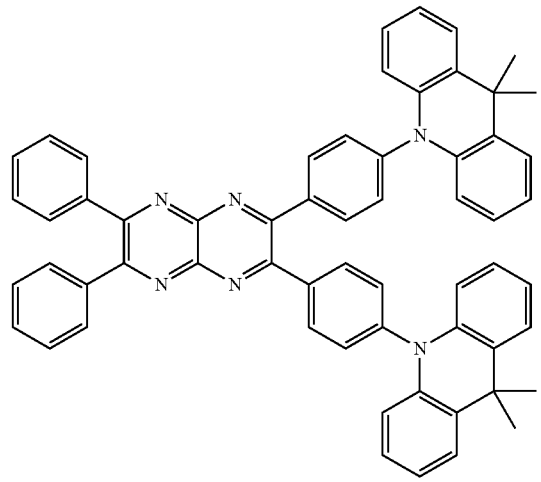

(3)

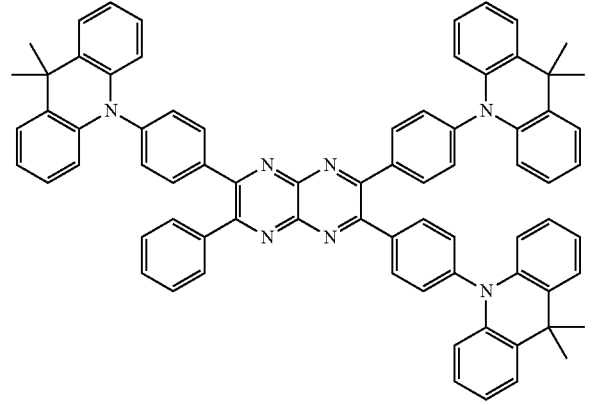

-continued (4)

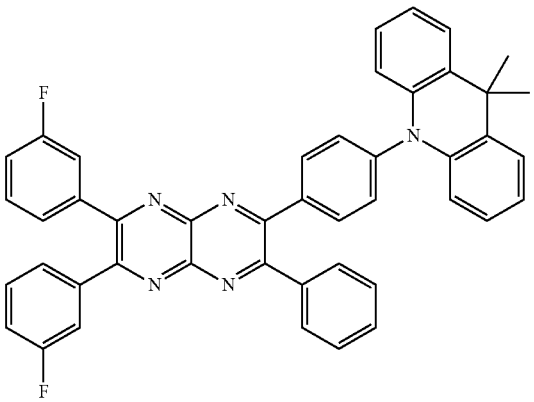

(5)

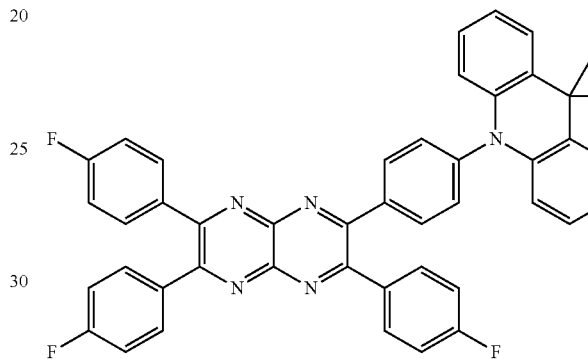

(6)

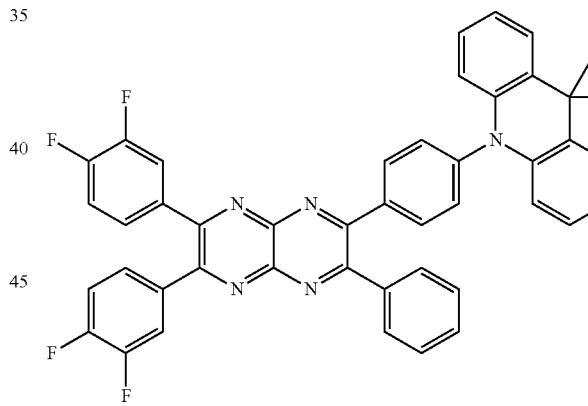

(7)

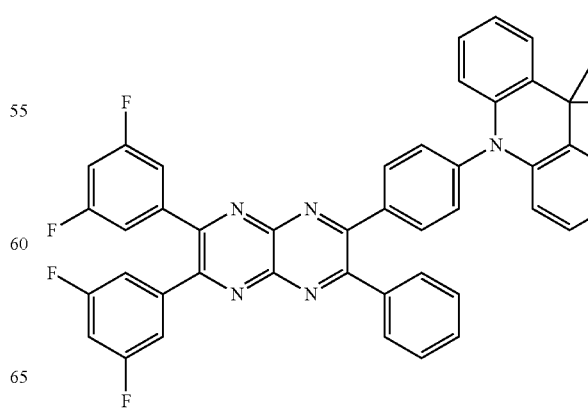

(8) (9) (10) (11) (12) (13) (14) (15)

(16)
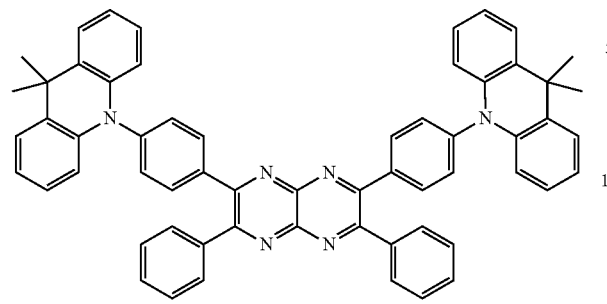
(17)
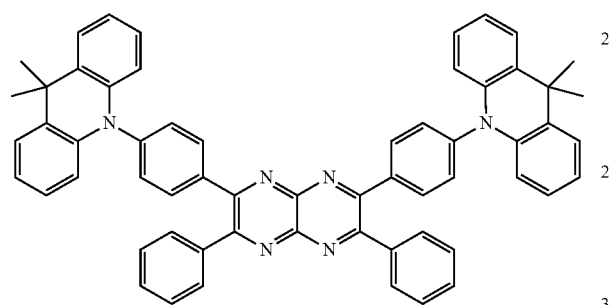
(18)
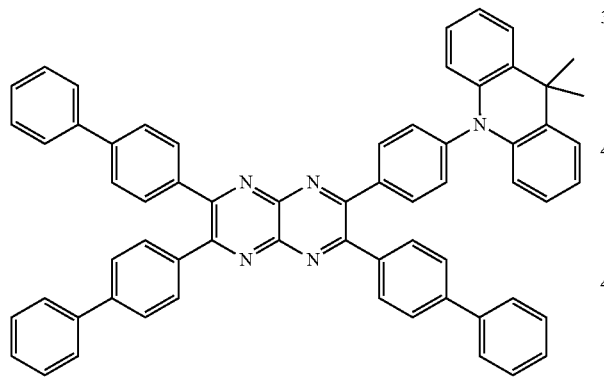
(19)
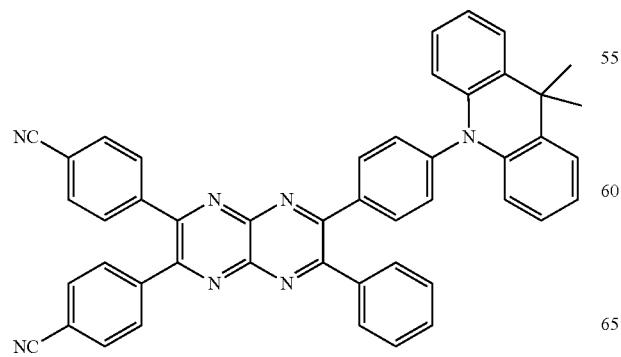
(20)
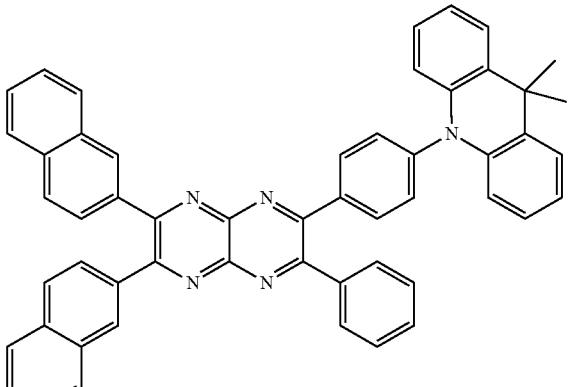
(21)
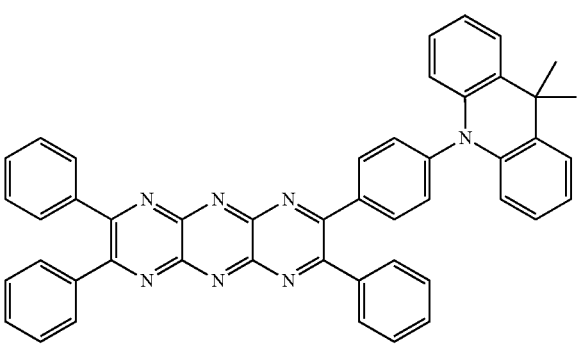
(22)
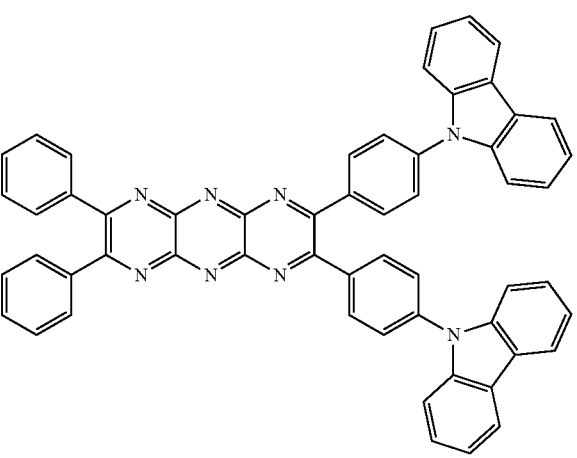
(23)
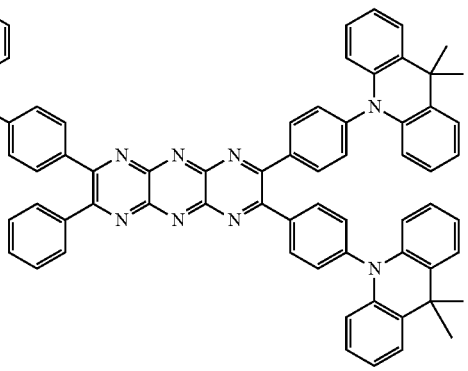

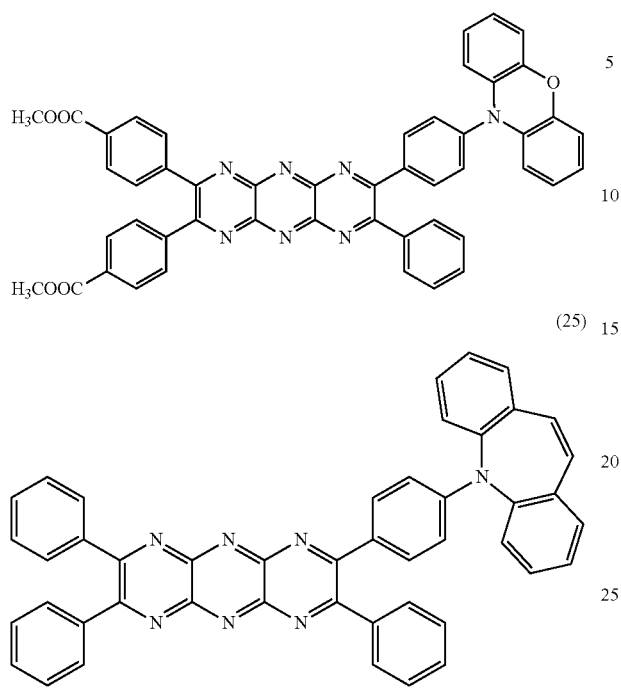

The molecular weight of the compound represented by the general formula (1) is preferably 1, 500 or less, more preferably 1,200 or less, further preferably 1,000 or less, and still further preferably 800 or less, for example, in the case where an organic layer containing the compound represented by the general formula (1) is intended to be formed as a film by a vapor deposition method. The lower limit of the molecular weight is the molecular weight of the compound represented by the general formula (1) that has the smallest molecular weight.

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used in a light-emitting layer of an organic light-emitting device.

For example, it may be considered that a polymer obtained by polymerizing a polymerizable monomer having the structure represented by the general formula (1) is used in a light-emitting layer of an organic light-emitting device. Specifically, it may be considered that a monomer that has a polymerizable functional group at any of $R^1$ to $R^{20}$ in the general formula (1) is prepared, and is homopolymerized or copolymerized with another monomer to prepare a polymer containing repeating units, and the polymer is used a light-emitting layer of an organic light-emitting device. In alternative, it may be considered that the compounds having a structure represented by the general formula (1) are reacted to form a dimer or a trimer, and the dimer or the trimer is used a light-emitting layer of an organic light-emitting device.

Examples of the structure of the repeating unit containing the structure represented by the general formula (1) include structures having a structure represented by the following general formula (21) or (22) in any of $R^1$ to $R^{20}$ in the general formula (1).

General Formula (21)

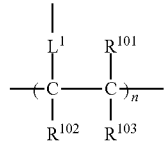

General Formula (22)

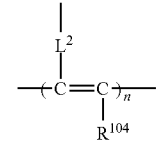

In the general formulae (21) and (22), $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by $-X^{11}-L^{11}-$, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (21) and (22), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

Specific examples of the structure of the repeating unit include structures having a structure represented by any of the following general formulae (23) to (26) in any of $R^1$ to $R^{20}$ in the general formula (1). Two or more of $R^1$ to $R^{20}$ each may contain the structure represented by any of the following general formulae (23) to (26), and it is preferred that only one of $R^1$ to $R^{20}$ contains the structure represented by any of the following general formulae (23) to (26).

General Formula (23)

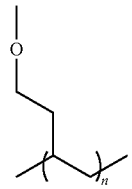

General Formula (24)

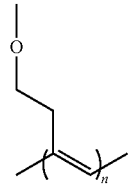

-continued

General Formula (25)

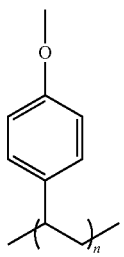

General Formula (26)

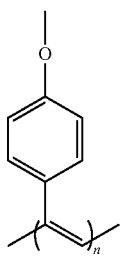

The polymer having the repeating unit containing the structure represented by any of the formulae (23) to (26) may be synthesized in such a manner that at least one of $R^1$ to $R^{20}$ in the structure represented by the general formula (1) is formed into a group having a hydroxyl group, and the hydroxyl group as a linker is reacted with the following compound to introduce a polymerizable group thereto, followed by polymerizing the polymerizable group.

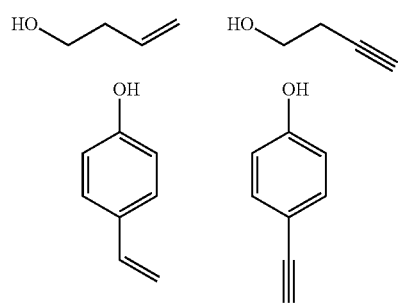

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds.

Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene.

Compound Represented by General Formula (11)

In the compound represented by the general formula (1), the compound represented by the general formula (11) is a novel compound.

General Formula (11)

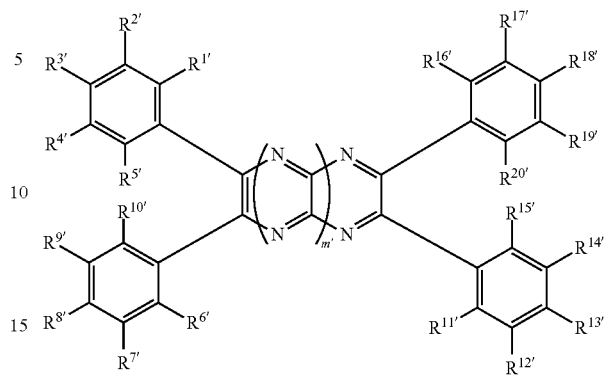

In the general formula (11), $R^{1'}$ to $R^{5'}$ each independently represent a hydrogen atom or a substituent having a Hammett $\sigma_p$ value of 0 or more; $R^{6'}$ to $R^{20'}$ each independently represent a hydrogen atom or a substituent, provided that at least one of $R^{6'}$ to $R^{20'}$ represents a substituted or unsubstituted N,N-diarylamino group; and m' represents 1 or 2.

For the descriptions and the preferred ranges of $R^{1'}$ to $R^{5'}$, $R^{6'}$ to $R^{20'}$, and m', reference may be made to the descriptions for the compound represented by the general formula (1).

The compound represented by the general formula (11) is preferably a compound represented by the following general formula (12):

General Formula (12)

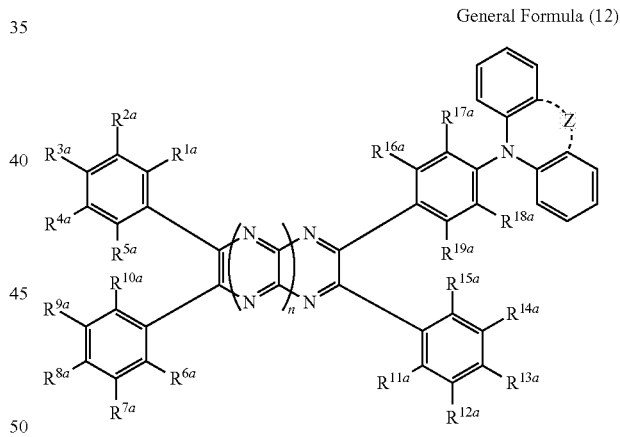

In the general formula (12), $R^{1a}$ to $R^{5a}$ and $R^{16a}$ to $R^{19a}$ each independently represent a hydrogen atom or a substituent having a Hammett $\sigma_p$ value of 0 or more; $R^{6a}$ to $R^{15a}$ each independently represent a hydrogen atom, a substituent having a Hammett $\sigma_p$ value of 0 or more, or a substituted or unsubstituted N,N-diarylamino group; n represents 1 or 2; and Z represents a linking group containing a carbon chain for forming a 6-membered or 7-membered ring, or an oxygen atom for forming a 6-membered ring.

For the descriptions and the preferred examples of the substituent that may be represented by $R^{1a}$ to $R^{5a}$ and $R^{16a}$ to $R^{19a}$, reference may be made to the descriptions and the preferred examples of the substituent that may be represented by $R^1$ to $R^5$ in the general formula (1), and among these, the substituent that is represented by $R^{1a}$ to $R^{5a}$ is preferably a fluorine atom. For the descriptions and the preferred ranges of the N,N-diarylamino group that may be represented by $R^{6a}$ to $R^{15a}$, reference may be made to the descriptions and the preferred ranges of the N,N-diarylamino group that may be represented by $R^6$ to $R^{20}$ in the general formula (1). n represents 1 or 2, and preferably 1. In the case where Z represents a carbon chain, the number of the carbon atom of the carbon chain is 1 or 2. When the number of the carbon atoms is 2, an unsaturated bond may intervene between the carbon atoms. The carbon chain may be substituted by a substituent. For the descriptions and the preferred ranges of the substituent, reference may be made to the descriptions and the preferred ranges of the substituent of the substituted aromatic group that may be represented by $Ar^1$ and $Ar^2$ in the general formula (2), and the like.

Synthesis Method of Compound Represented by General Formula (11)

The synthesis method of the compound represented by the general formula (11) is not particularly limited. The compound represented by the general formula (11) may be synthesized by combining the known synthesis methods and conditions.

For example, the compound represented by the general formula (11), in which $R^{18'}$ represents a group represented by the general formula (3), and m represents 1, can be synthesized according to the following scheme.

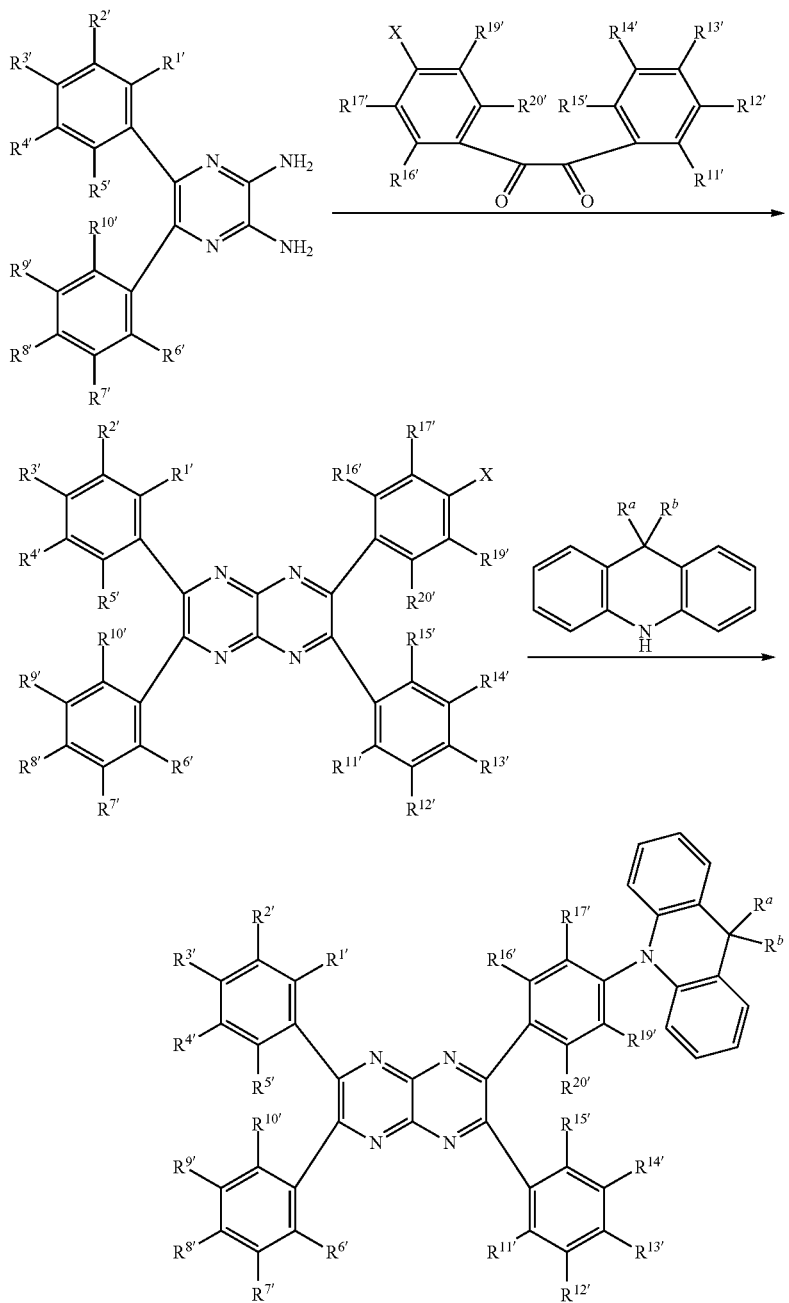

In the scheme $R^{1'}$ to $R^{17'}$, $R^{19'}$, and $R^{20'}$ have the same meanings as in the general formula (11), $R^a$ and $R^b$ have the same meanings as in the general formula (3), and X represents a halogen atom. Examples of the halogen atom include a fluorine atom, a chlorine atom, a bromine atom, and an iodine atom, and a fluorine atom, a chlorine atom, and a bromine atom are preferred. The reaction conditions and procedures of the reaction steps used may be appropriately selected from the known reaction conditions and procedures that have been used in the analogous synthesis reaction.

The compound represented by the general formula (11) except for the compound, in which $R^{18'}$ represents a group represented by the general formula (3), and m represents 1, can be synthesized by modifying the aforementioned scheme. For the details of the reactions, reference may be made to the synthesis examples described later. The compound represented by the general formula (11) may also be synthesized by combining the other known synthesis reactions.

Organic Light-Emitting Device

The compound represented by the general formula (1) of the invention is useful as a light-emitting material of an organic light-emitting device. Accordingly, the compound represented by the general formula (1) of the invention may be effectively used as a light-emitting material in a light-emitting layer of an organic light-emitting device. The compound represented by the general formula (1) includes a delayed fluorescent emitter emitting delayed fluorescent light. Thus, the invention provides an invention relating to a delayed fluorescent emitter having the structure represented by the general formula (1), an invention relating to the use of the compound represented by the general formula (1) as the delayed fluorescent emitter, and an invention relating to a method for emitting delayed fluorescent light with the compound represented by the general formula (1). An organic light-emitting device that uses the compound as a light-emitting material has features that the device emits delayed fluorescent light and has a high light emission efficiency. The principle of the features may be described as follows for an organic electroluminescent device as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent emitter emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent emitter emitting light through absorption of thermal energy is particularly useful for an organic electroluminescent device. In the case where a delayed fluorescent emitter is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light-emitting material of a light-emitting layer may provide an excellent organic light-emitting device, such as an organic photoluminescent device (organic PL device) and an organic electroluminescent device (organic EL device). At this time, the compound represented by the general formula (1) of the invention may have a function of assisting light emission of another light-emitting material contained in the light-emitting layer, i.e., as a so-called assist dopant. Specifically, the compound represented by the general formula (1) of the invention contained in the light-emitting layer may have a lowest excited singlet energy level that is between the lowest excited singlet energy level of the host material contained in the light-emitting layer and the lowest excited singlet energy level of the another light-emitting material contained in the light-emitting layer.

The organic photoluminescent device has a structure containing a substrate having formed thereon at least a light-emitting layer. The organic electroluminescent device has a structure containing at least an anode, a cathode and an organic layer formed between the anode and the cathode. The organic layer contains at least a light-emitting layer, and may be formed only of a light-emitting layer, or may have one or more organic layer in addition to the light-emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material, a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness thereof may be generally selected from a range of from 10 to 1,000 nm, and preferably from 10 to 200 nm, while depending on the material used.

Cathode

The cathode is preferably formed of as an electrode material, a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light-emitting material, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light-emitting layer but also in the other layers than the light-emitting layer. In this case, the compound represented by the general formula (1) used in the light-emitting layer and the compound represented by the general formula (1) used in the other layers than the light-emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_2$ to $R_7$ each independently represent a hydrogen atom or a substituent, and n represents an integer of from 3 to 5.
Preferred examples of a compound that may also be used as the host material of the light-emitting layer are shown below.
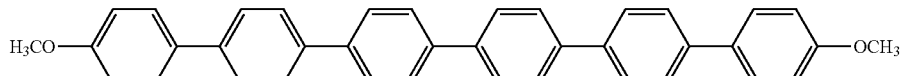
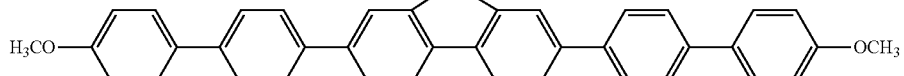
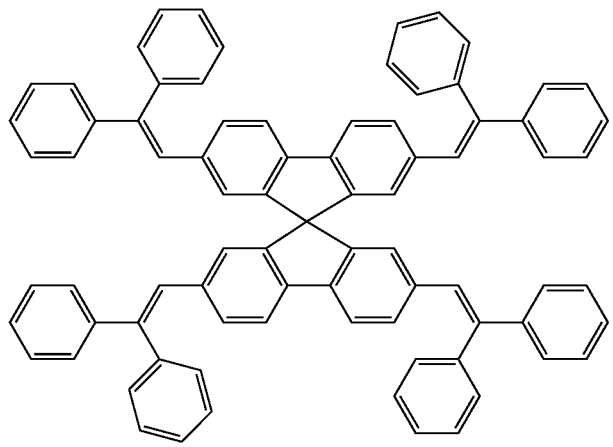
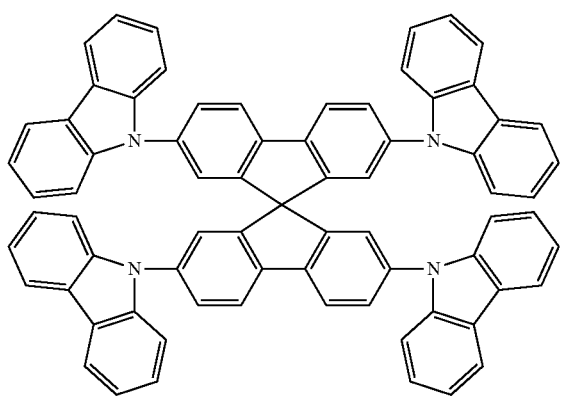
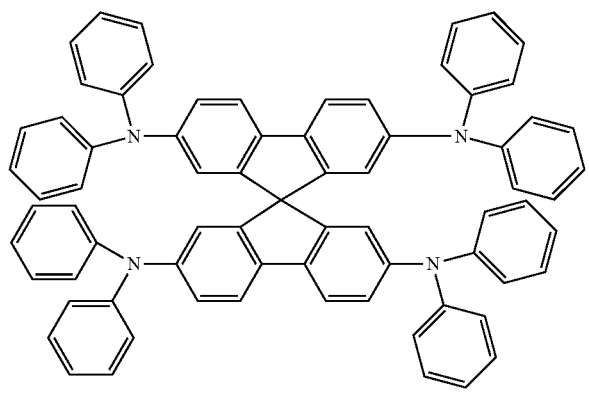
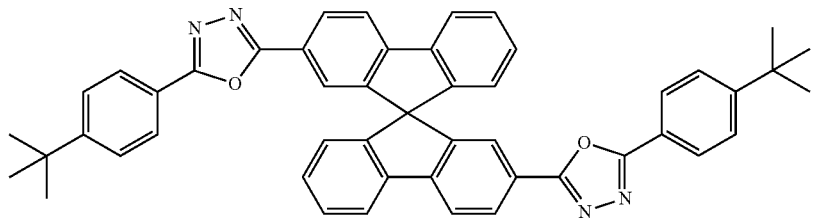

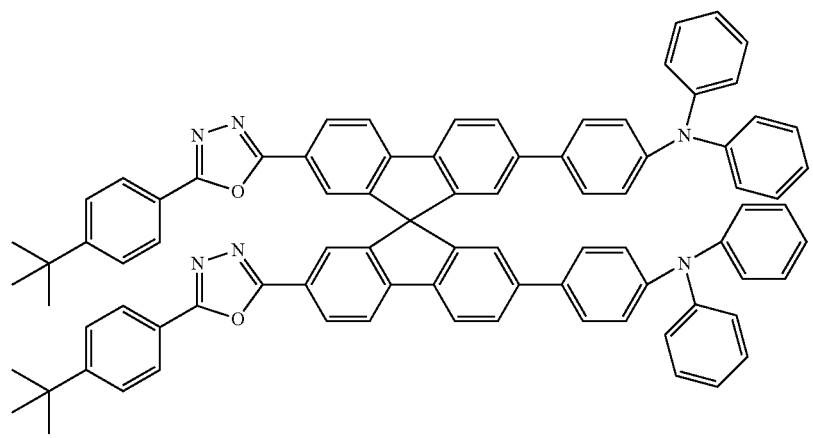
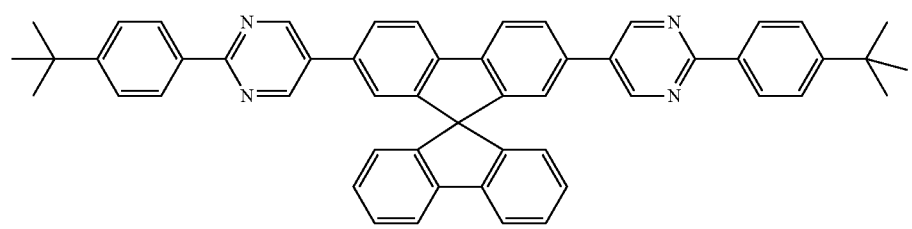
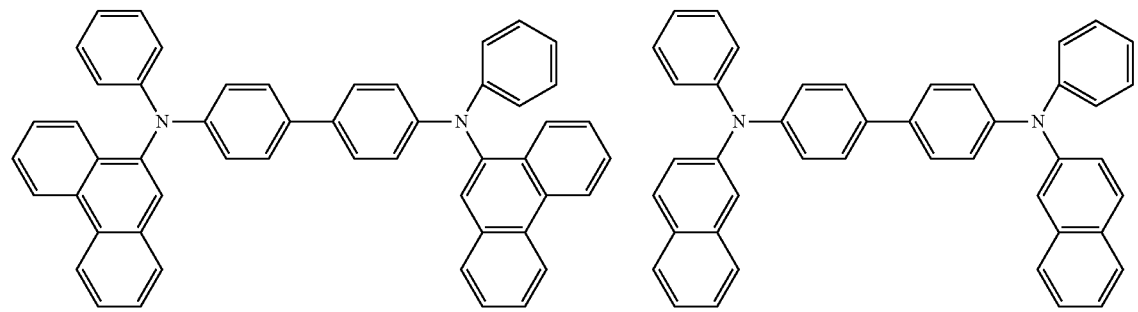
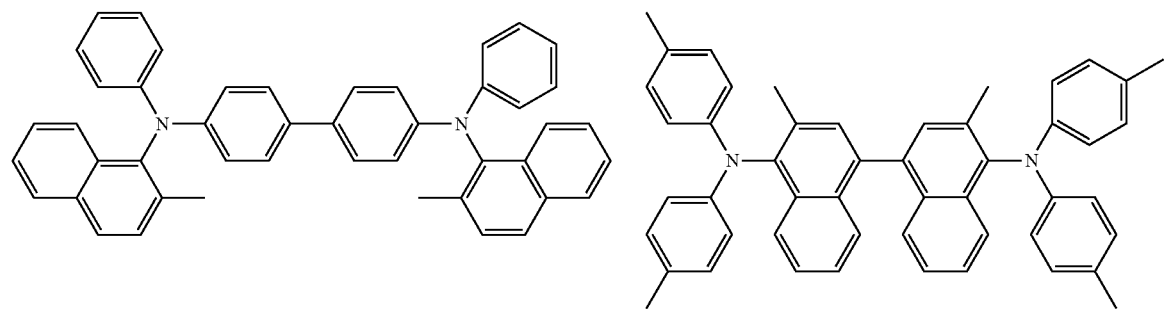

-continued
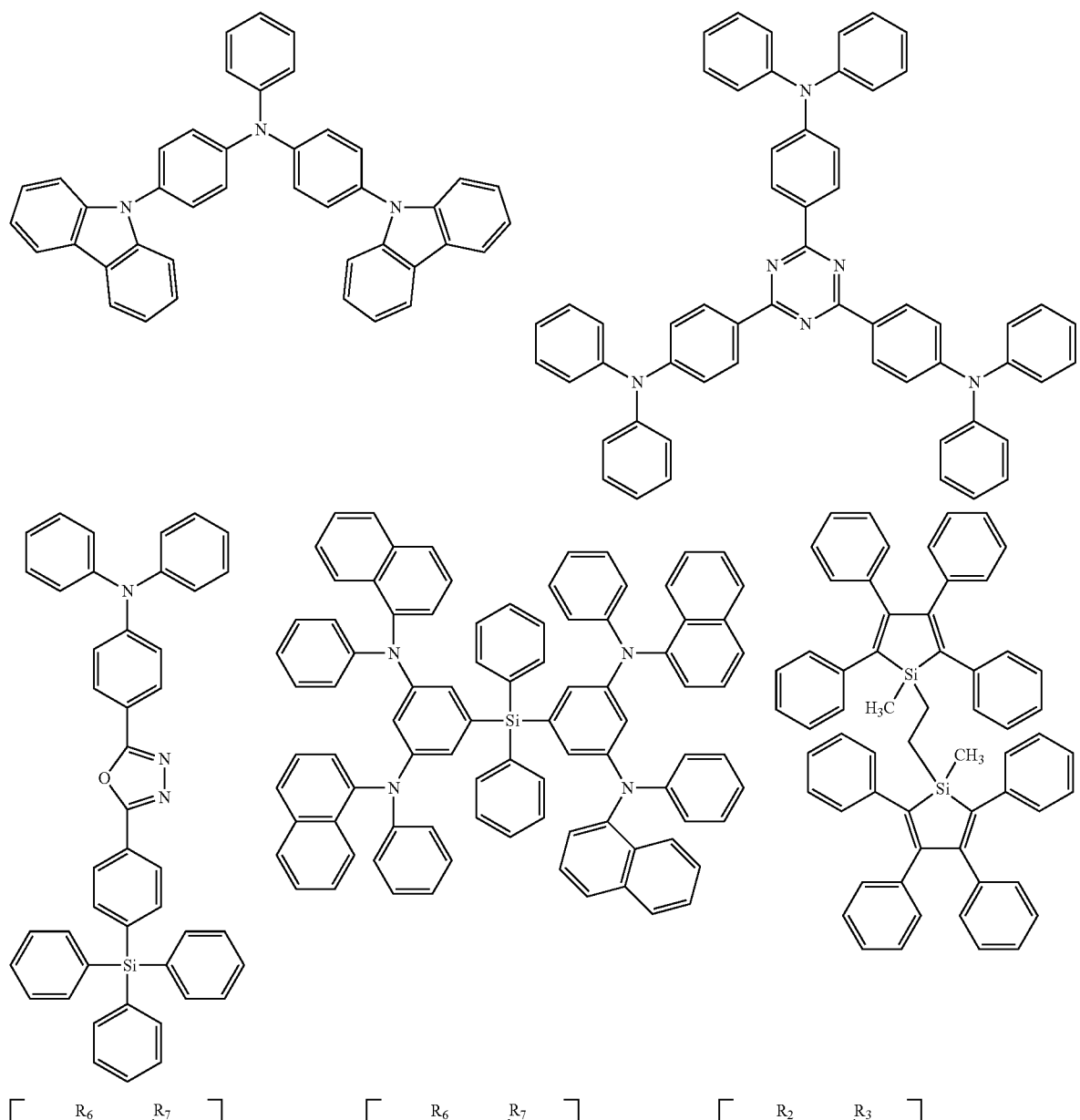
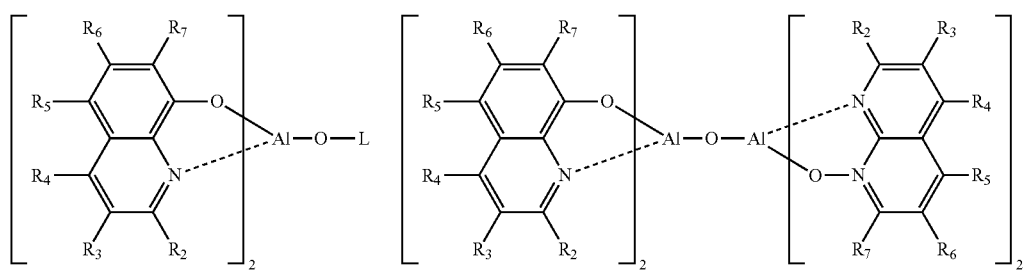
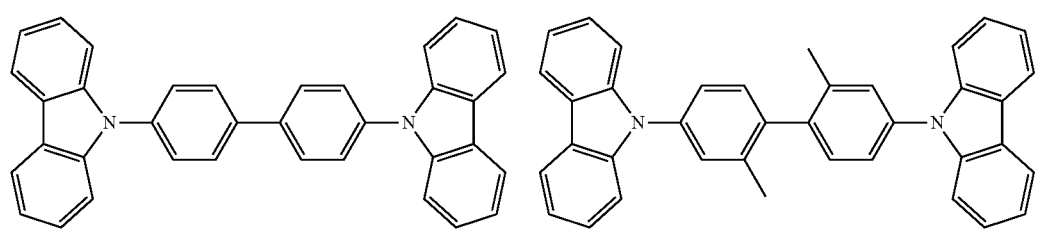

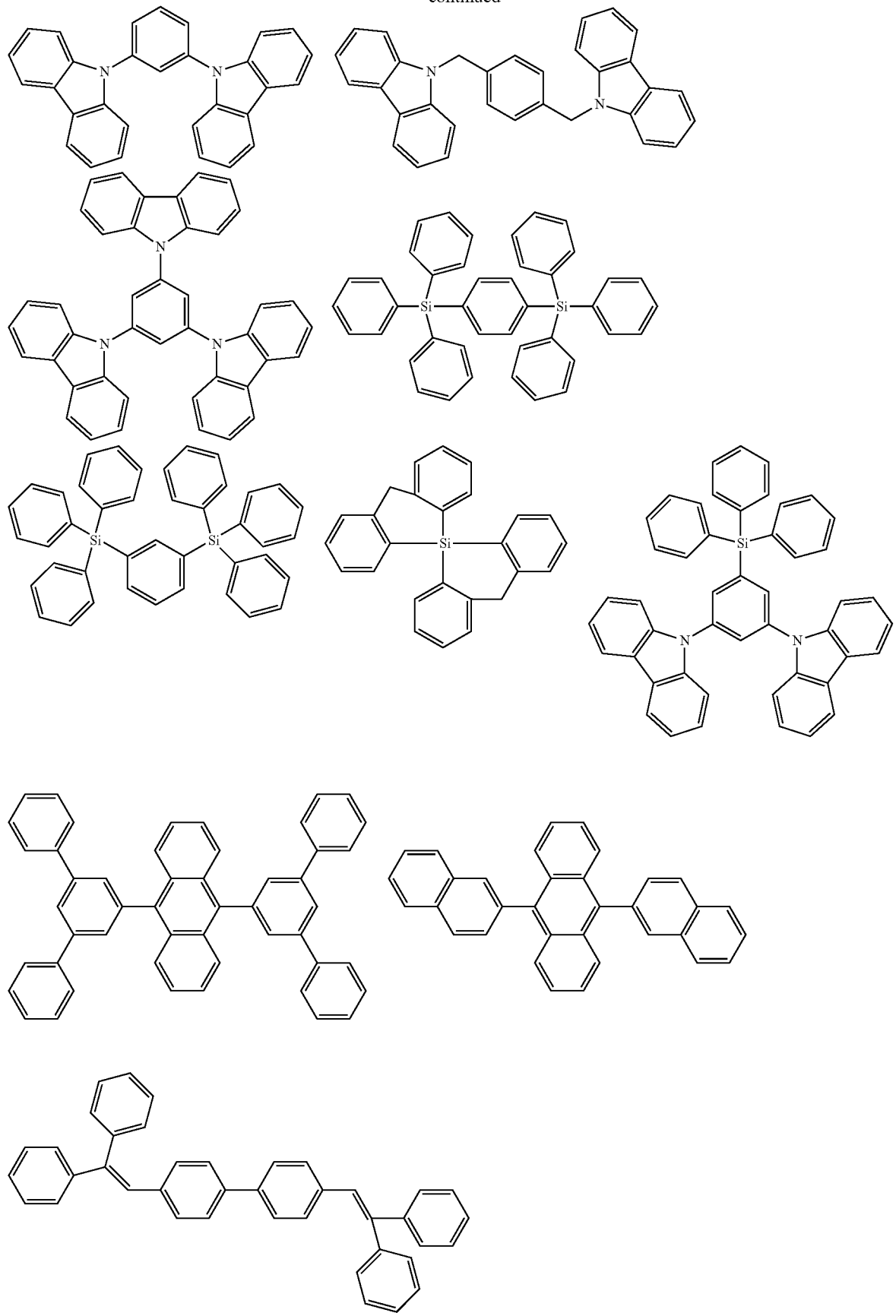

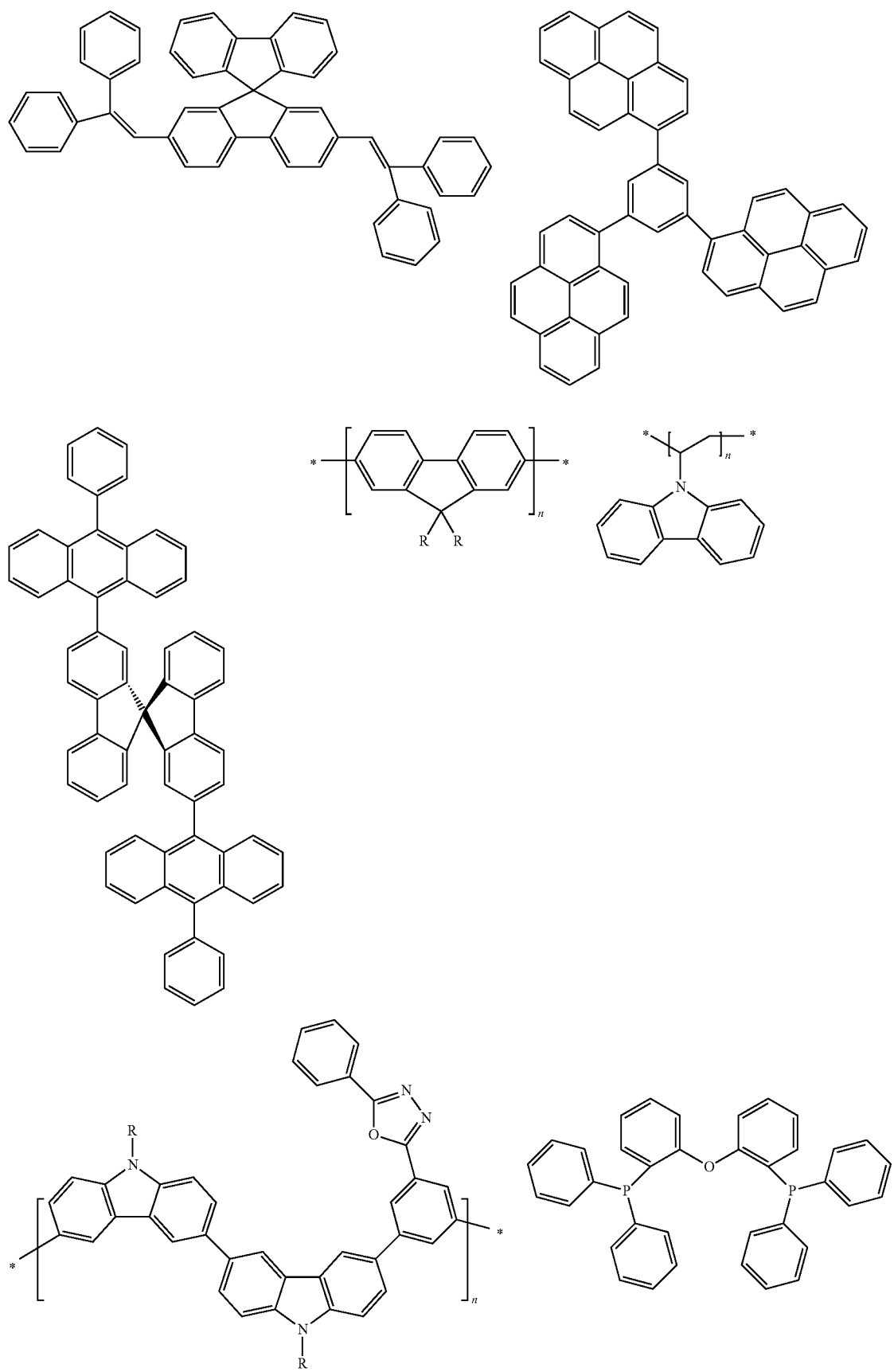

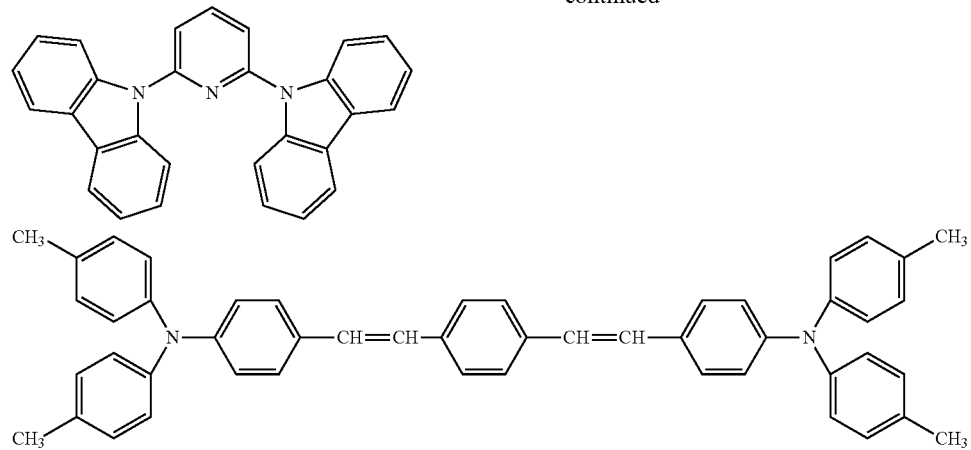
Preferred examples of a compound that may be used as the hole injection material are shown below.
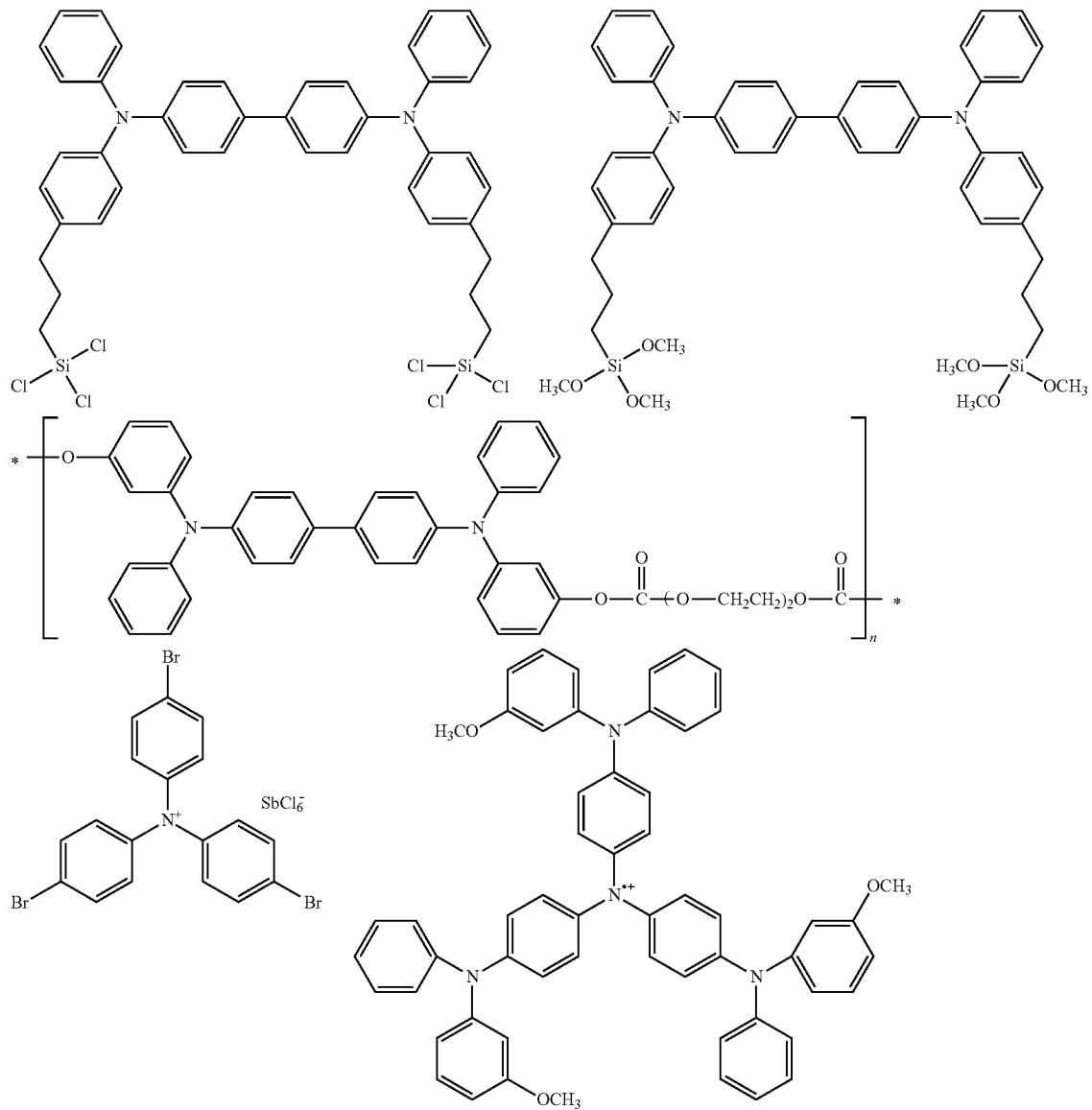

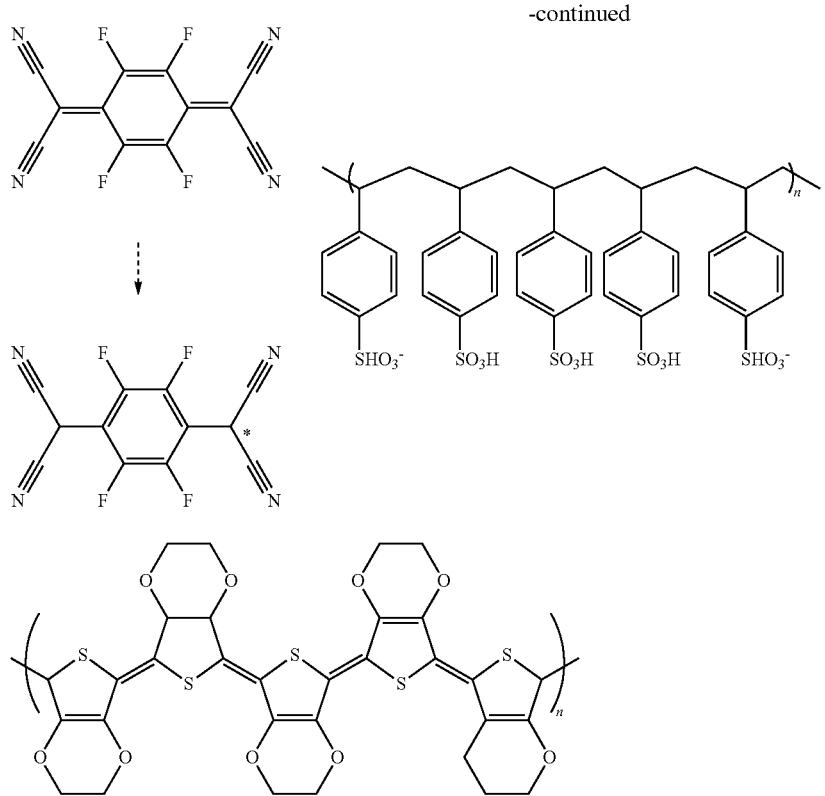
Preferred examples of a compound that may be used as the hole transporting material are shown below.
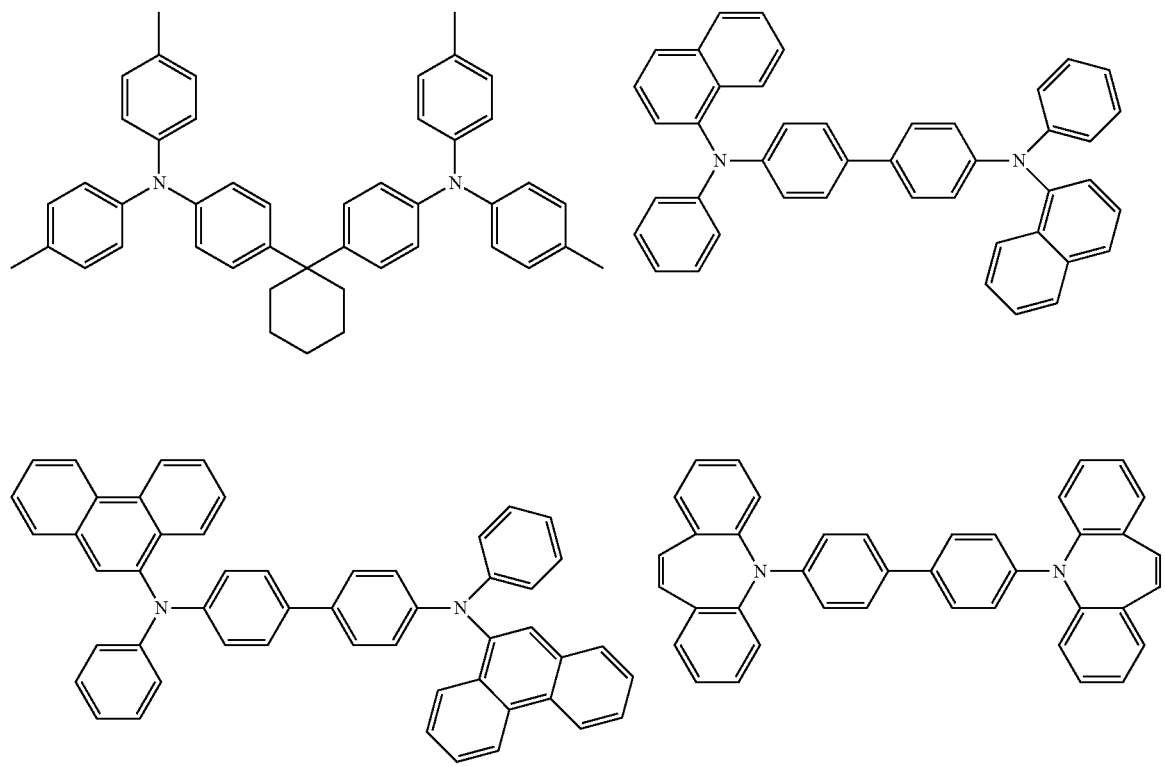

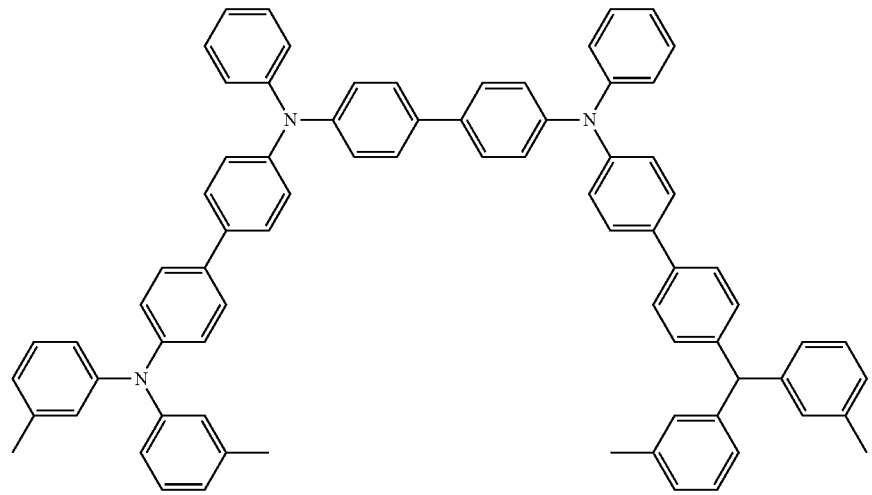
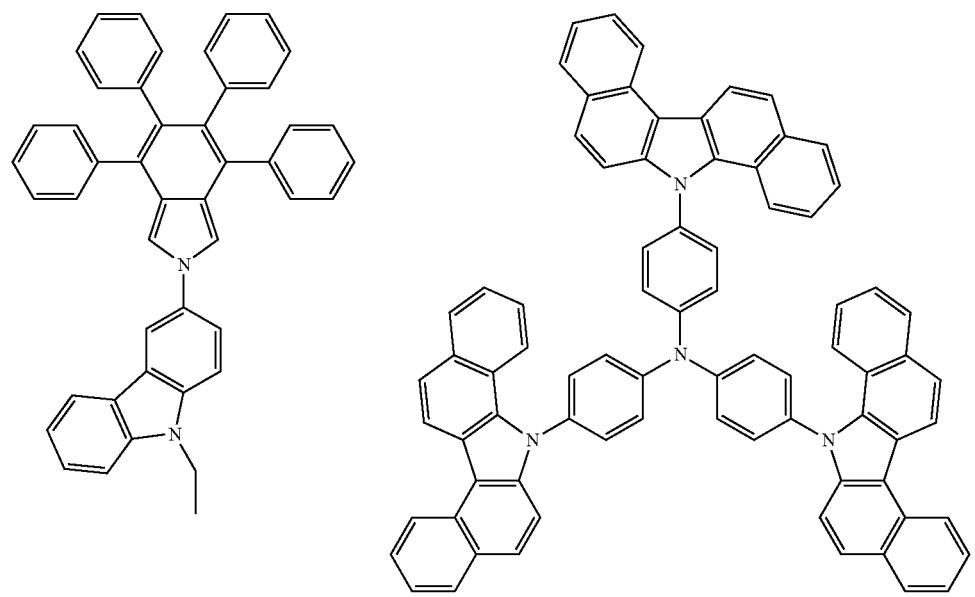
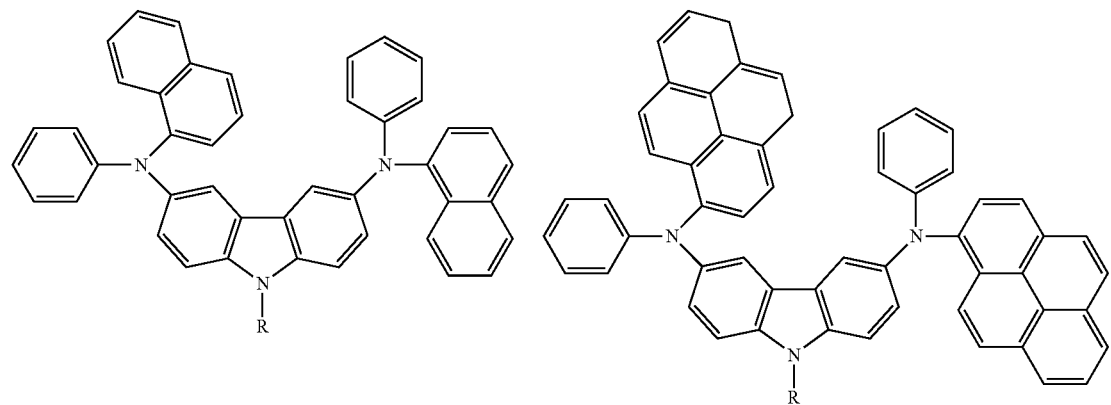

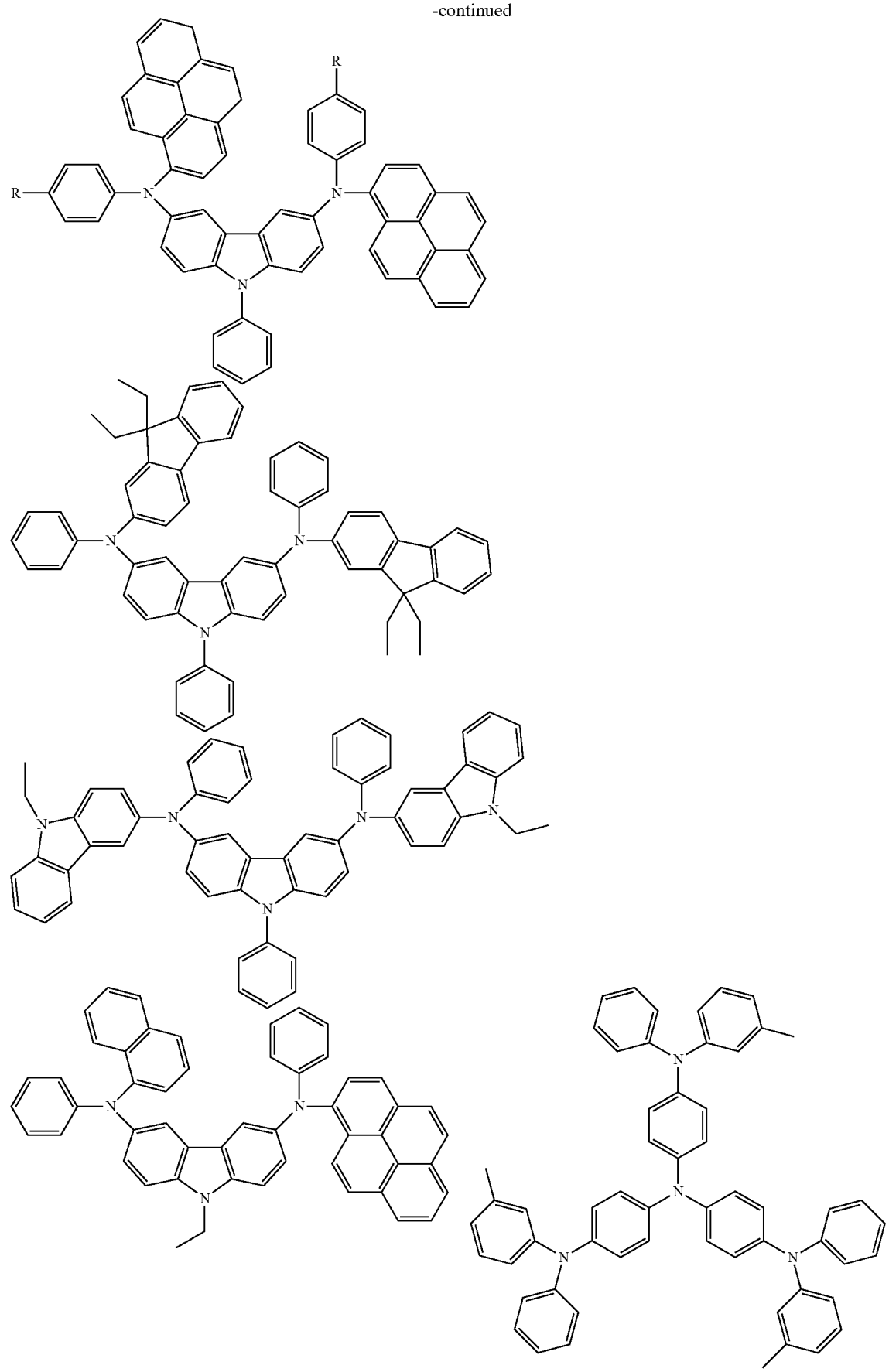

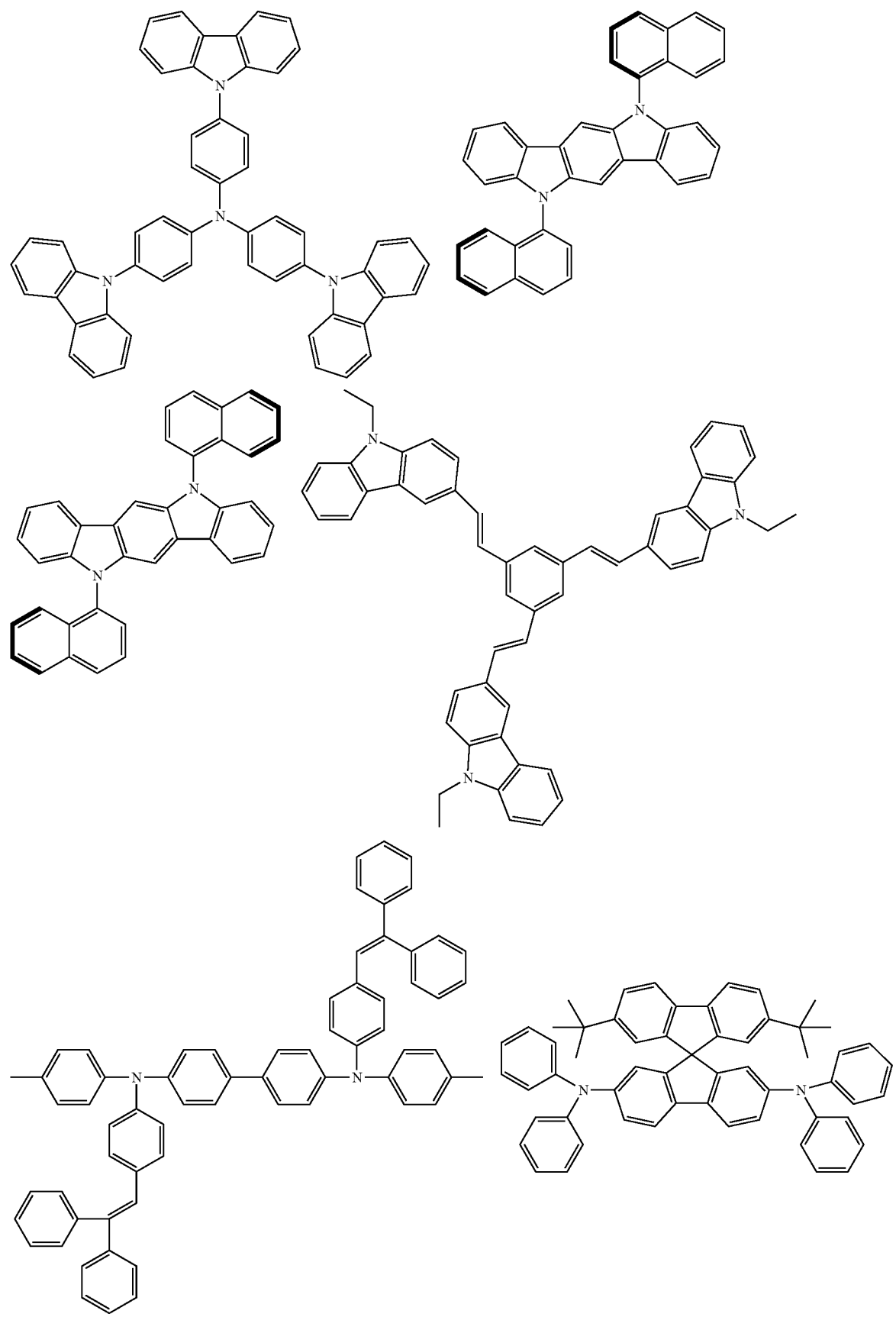

-continued
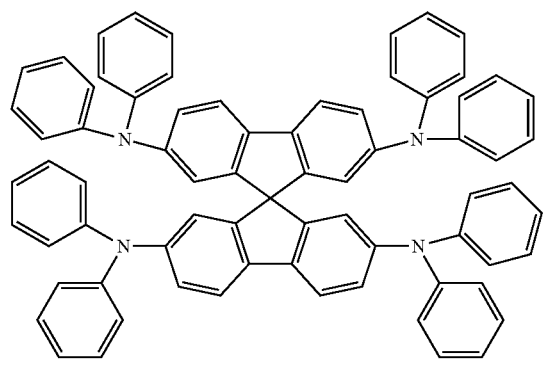
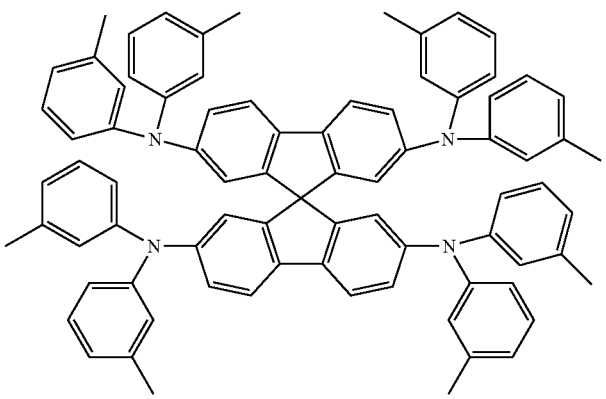
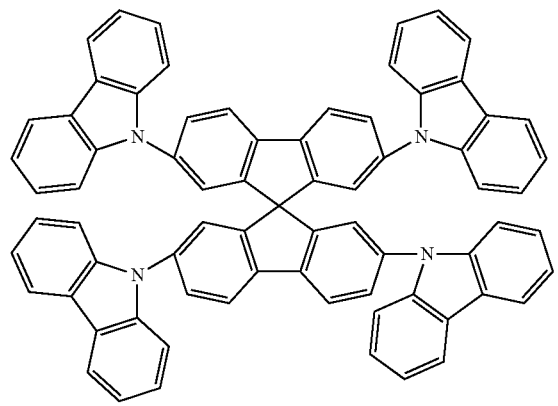
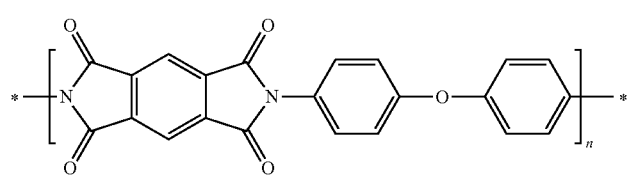
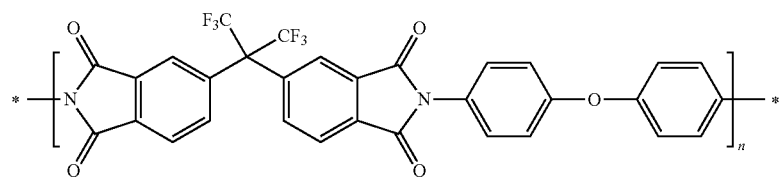
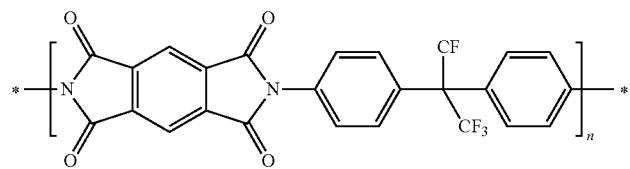
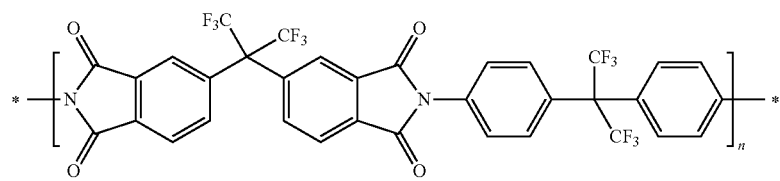
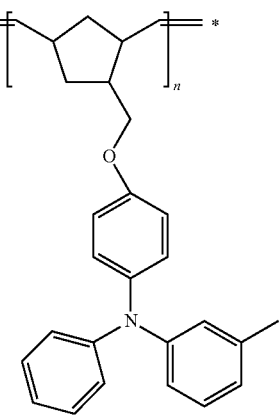

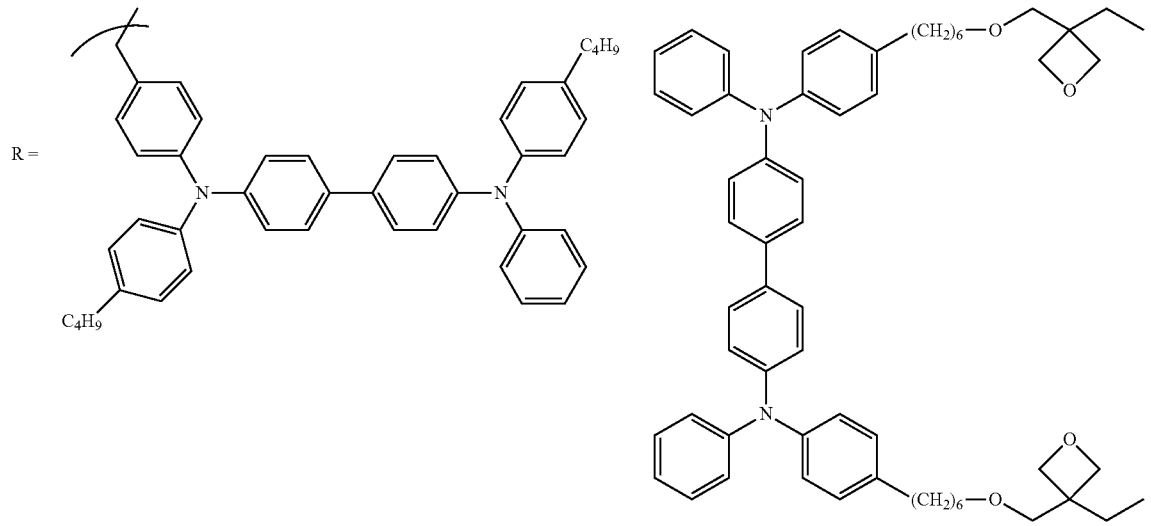
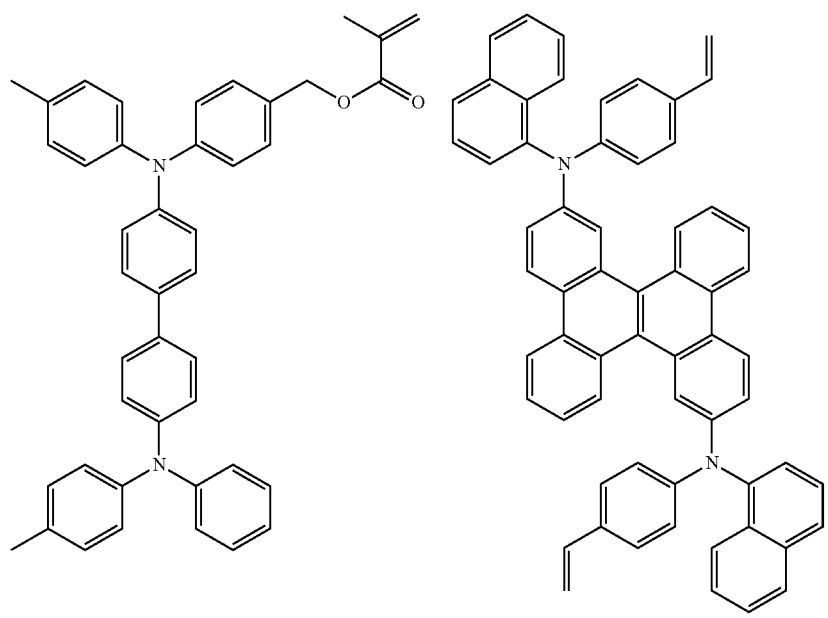
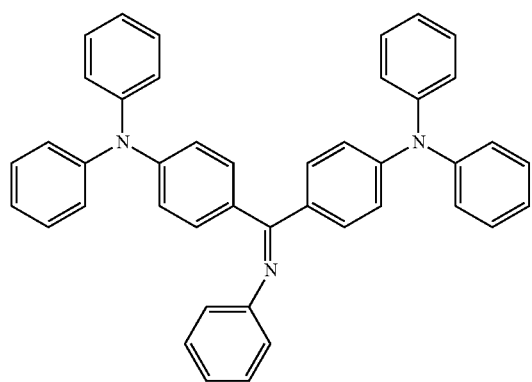

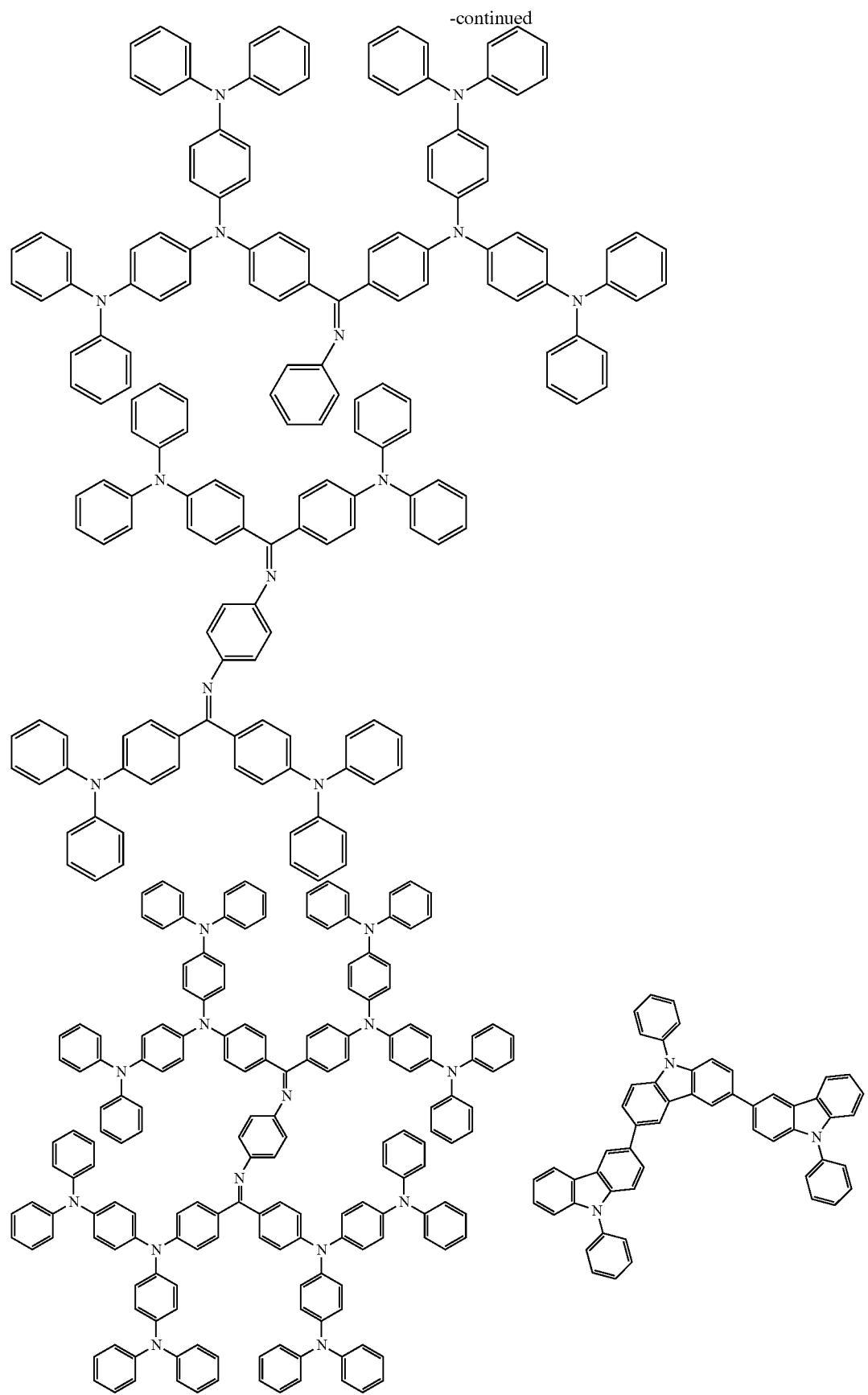

Preferred examples of a compound that may be used as the electron barrier material are shown below.
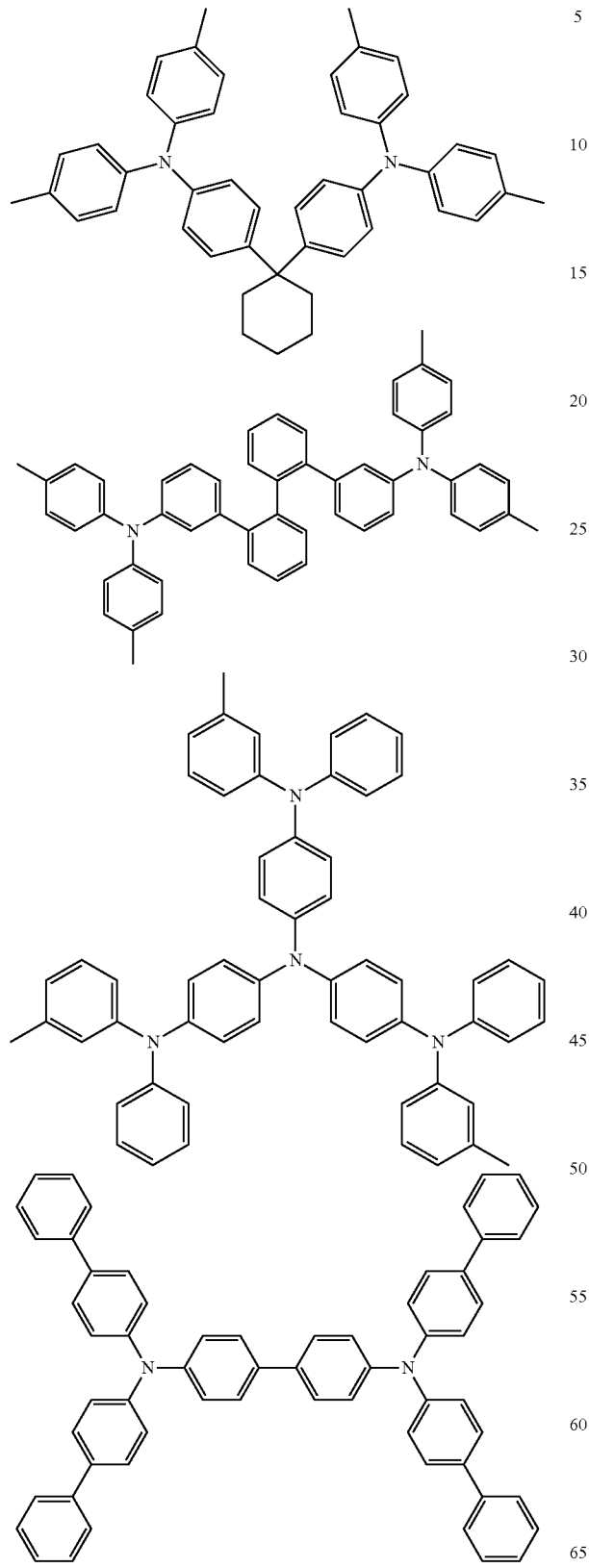
Preferred examples of a compound that may be used as the hole barrier material are shown below.
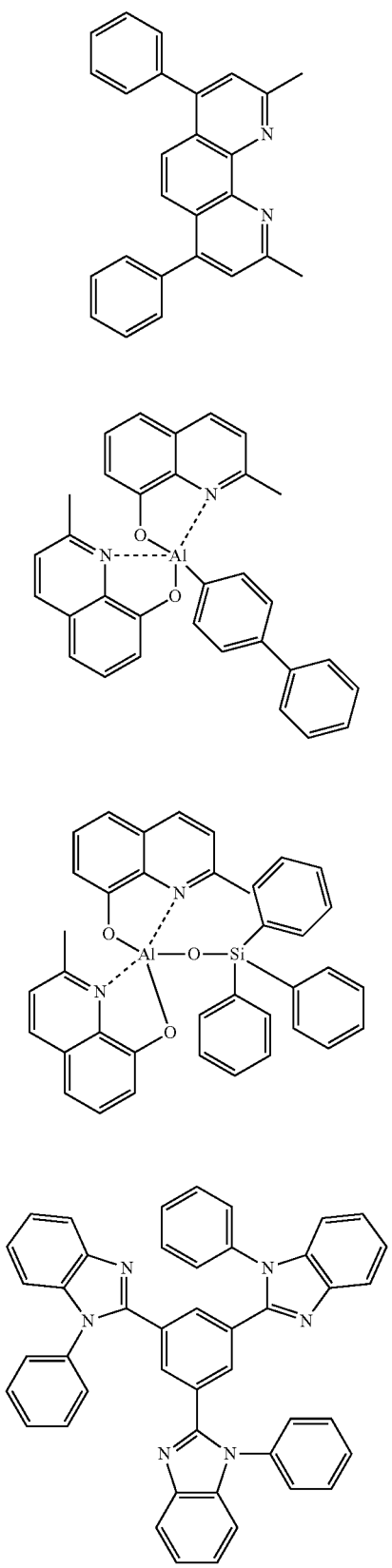

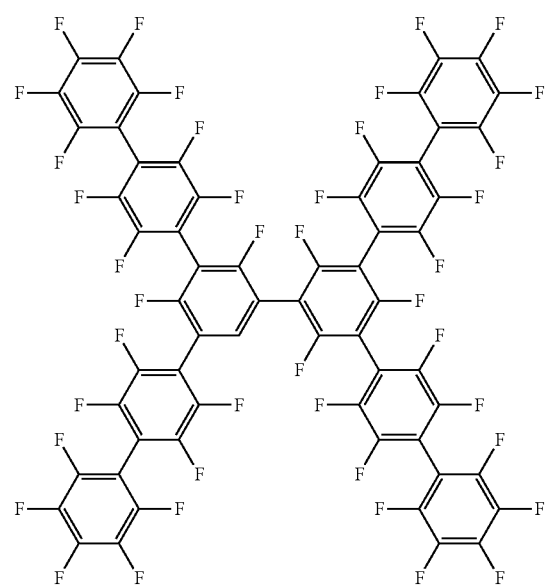
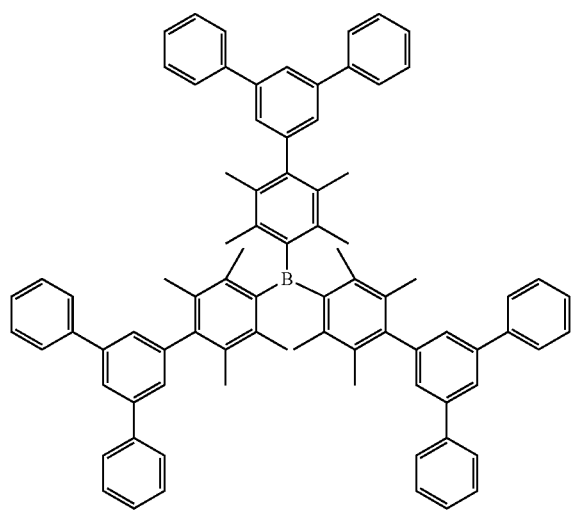
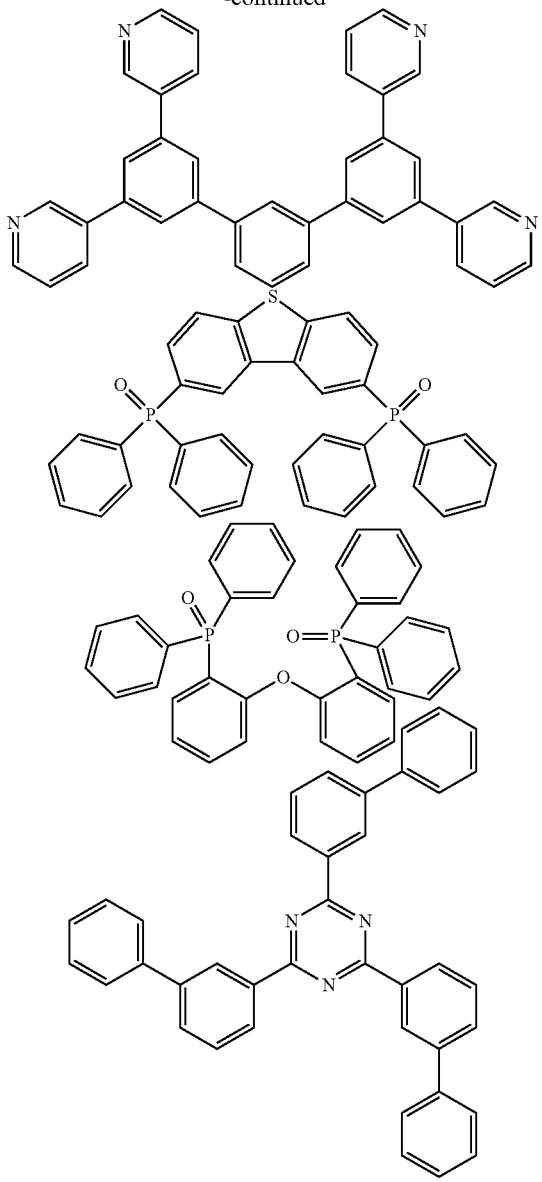
Preferred examples of a compound that may be used as the electron transporting material are shown below.
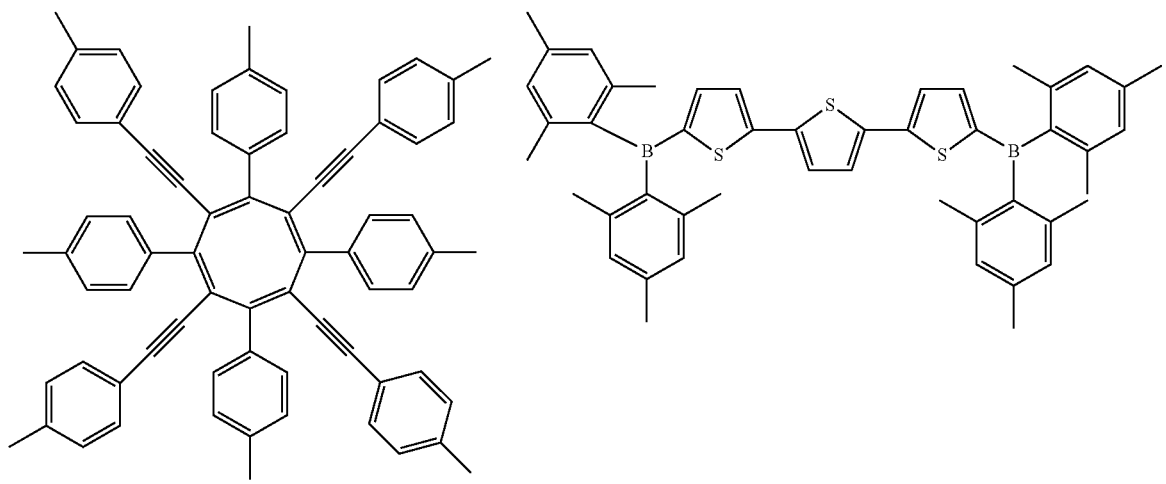

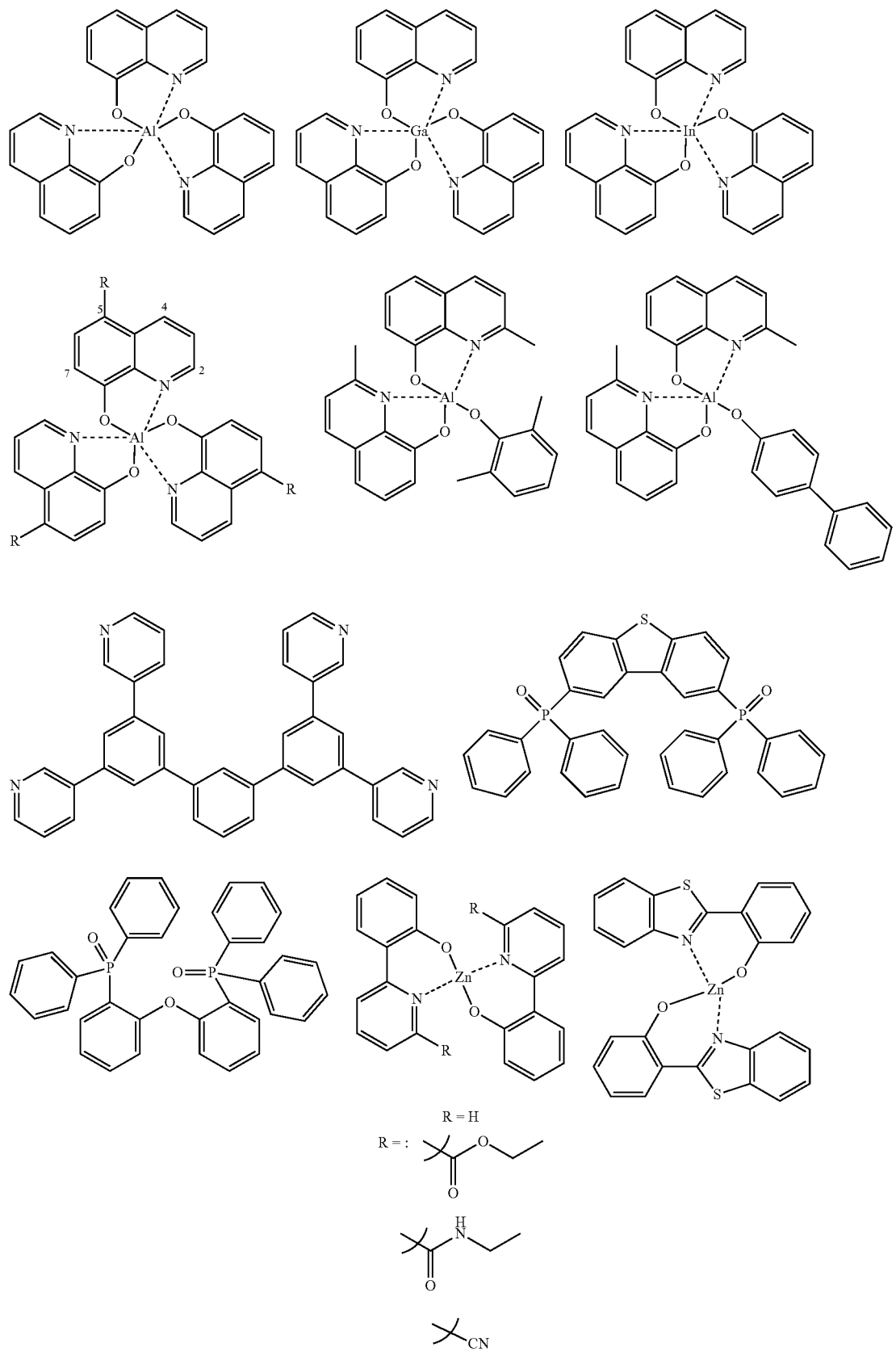

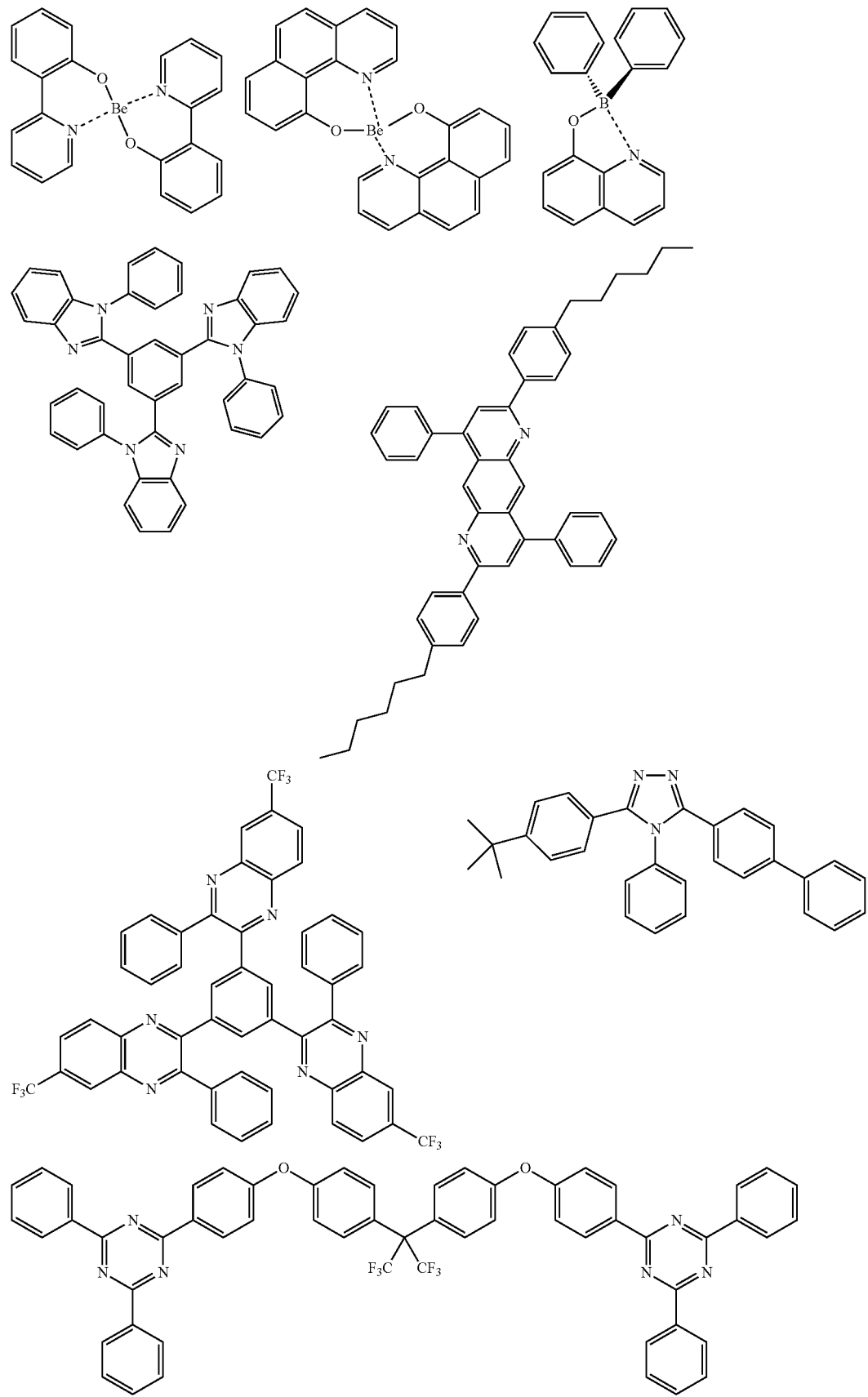

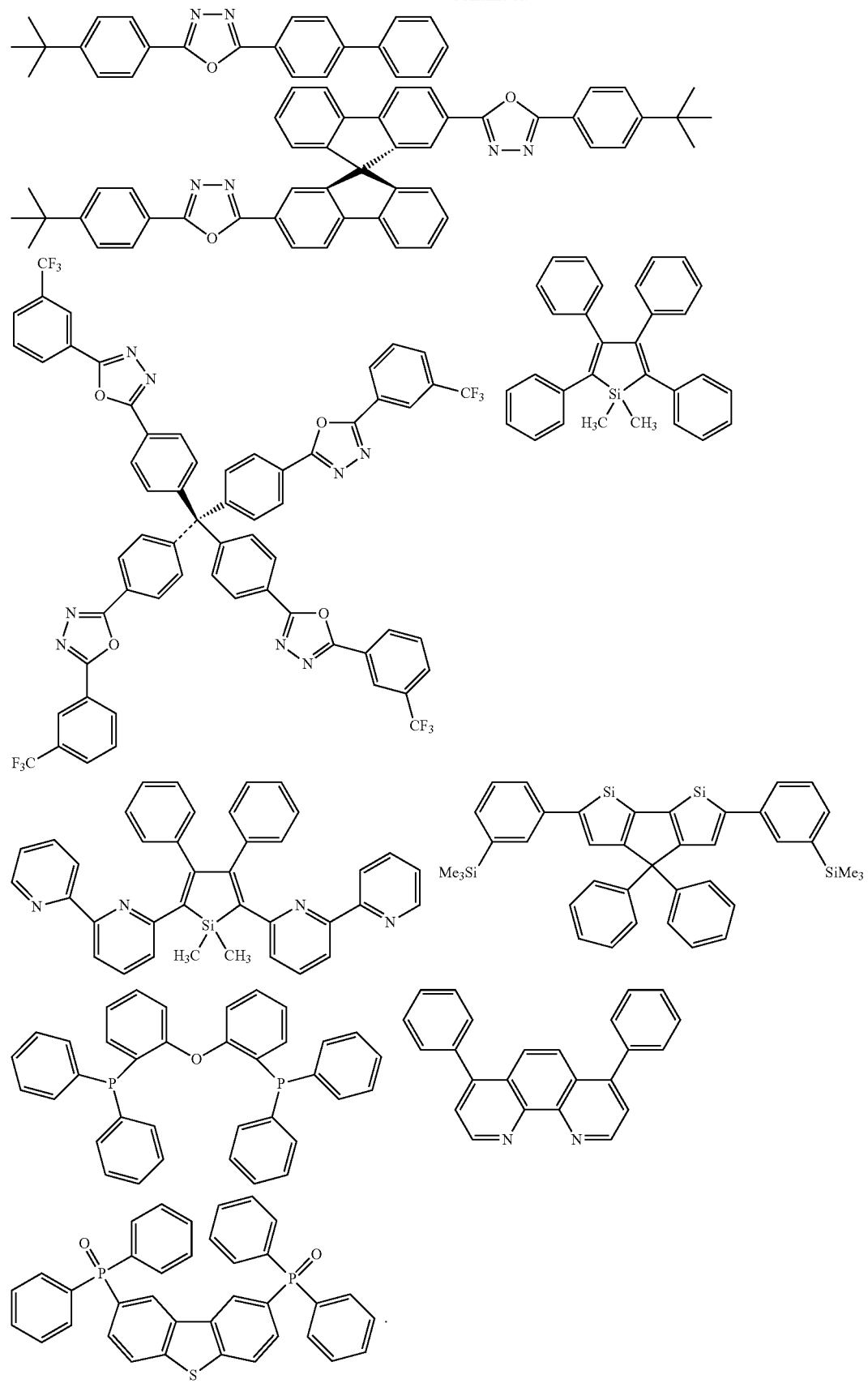

Preferred examples of a compound that may be used as the electron injection material are shown below.

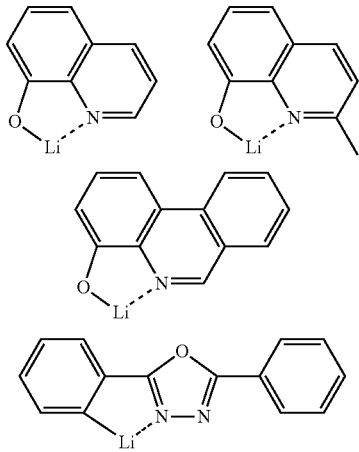

Preferred examples of a compound as a material that may be added are shown below. For example, the compound may be added as a stabilizing material.

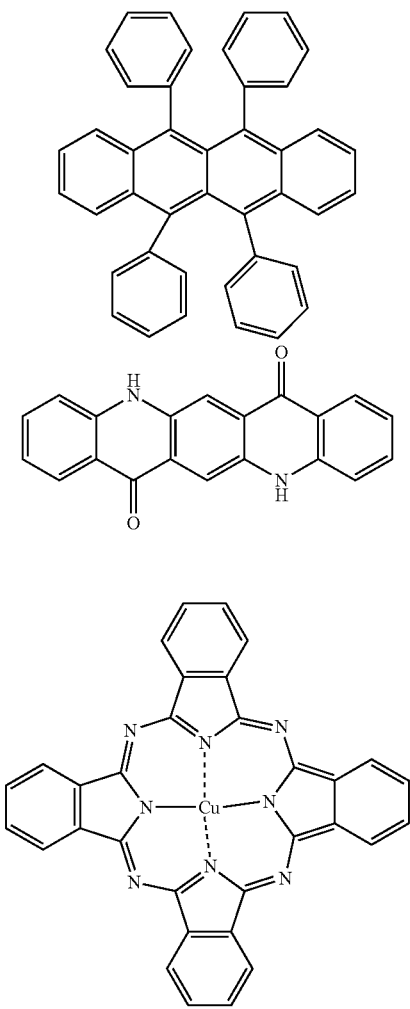

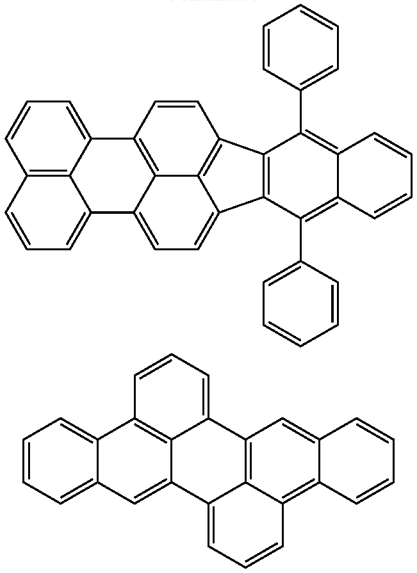

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below. The light emission characteristics were evaluated by using a source meter (2400 Series, produced by Keithley Instruments Inc.), a semiconductor parameter analyzer (E5273A, produced by Agilent Technologies, Inc.), an optical power meter (1930C, produced by Newport Corporation), an optical spectrometer (USB2000, produced by Ocean Optics, Inc.), a spectroradiometer (SR-3, produced by Topcon Corporation), and a streak camera (Model C4334, produced by Hamamatsu Photonics K.K.).

The difference ($\Delta E_{ST}$) between the singlet energy ($E_{S1}$) and the triplet energy ($E_{T1}$) of the materials was obtained in such a manner that the singlet energy ($E_{S1}$) and the triplet energy ($E_{T1}$) were calculated in the following manners, and the difference was obtained by the expression, $\Delta E_{ST} = E_{S1} - E_{T1}$.

(1) Singlet Energy $E_{S1}$

The compound to be measured and mCBP were vapor-co-deposited to a thickness of 100 nm on a Si substrate to make a concentration of the compound to be measured of 6% by weight, which was designated as a specimen. The specimen was measured for a fluorescence spectrum at ordinary temperature (300 K). The light emission was accumulated from immediately after the incidence of excitation light to after 100 nsec from the incidence, thereby providing a fluorescence spectrum with the light emission intensity as the ordinate and the wavelength as the abscissa. In the fluorescence spectrum, the ordinate was the light emission, and the abscissa was the wavelength. A tangent line was drawn for the rising part of the photoluminescence spectrum on the short wavelength side, and the wavelength λedge (nm) of the intersection point of the tangent line and the abscissa was obtained. The wavelength value was converted to an energy value according to the following conversion expression to provide the singlet energy $E_{S1}$.

$E_{S1}$ (eV)=1,239.85/λedge  Conversion Expression

The photoluminescence spectrum was measured with a nitrogen laser (MNL200, produced by Lasertechnik Berlin GmbH) as an excitation light source and a streak camera (C4334, produced by Hamamatsu Photonics K.K.) as a detector.

(2) Triplet Energy $E_{T1}$

The same specimen as used for the singlet energy $E_{S1}$ was cooled to 5 K, the specimen for measuring phosphorescent light was irradiated with excitation light (337 nm), and the phosphorescence intensity was measured with a streak camera. The light emission was accumulated from after 1 msec from the incidence of excitation light to after 10 msec from the incidence, thereby providing a phosphorescence spectrum with the phosphorescence intensity as the ordinate and the wavelength as the abscissa. A tangent line was drawn for the upstanding part of the phosphorescence spectrum on the short wavelength side, and the wavelength λedge (nm) of the intersection point of the tangent line and the abscissa was obtained. The wavelength value was converted to an energy value according to the following conversion expression to provide the singlet energy $E_{T1}$.

$E_{T1}$ (eV)=1,239.85/λedge  Conversion Expression

The tangent line for the upstanding part of the phosphorescence spectrum on the short wavelength side was drawn in the following manner. Over the range in the phosphorescence spectrum curve of from the short wavelength end to the maximum peak value closest to the short wavelength end among the maximum peak values of the spectrum, a tangent line was assumed while moving within the range toward the long wavelength side. The gradient of the tangent line was increased while the curve was standing up (i.e., the value of the ordinate was increased). The tangent line that was drawn at the point where the gradient thereof became maximum was designated as the tangent line for the upstanding part of the phosphorescence spectrum on the short wavelength side.

A maximum peak having a peak intensity that was 10% or less of the maximum peak intensity of the spectrum was not included in the maximum peak values and thus was not designated as the maximum peak value closest to the short wavelength end, and the tangent line that was drawn at the point where the gradient became maximum that was closest to the maximum peak value closest to the short wavelength end was designated as the tangent line for the upstanding part of the phosphorescence spectrum on the short wavelength side.

Synthesis Example 1

Synthesis of Example Compound (1)

In this synthesis example, the example compound (1) was synthesized according to the following scheme.

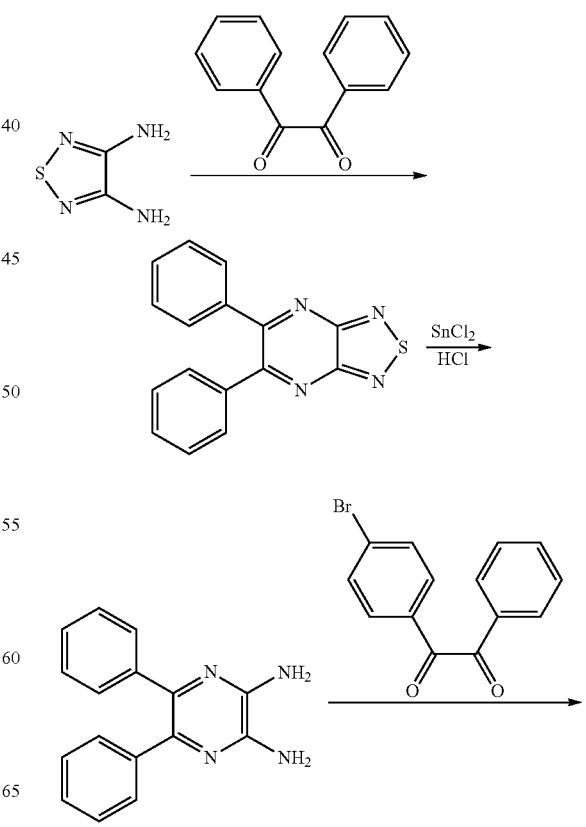

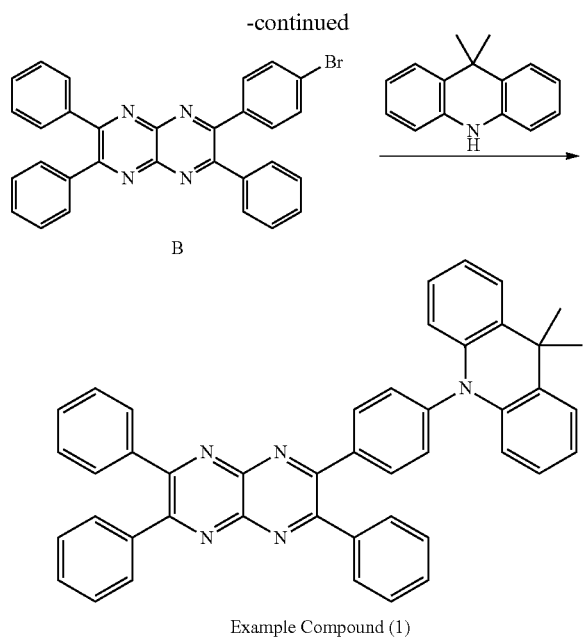

B

Example Compound (1)

(1) Synthesis Process of 2,3-Diamino-5,6-diphenylpyrazine 2,3-Diamino-5,6-diphenylpyrazine was synthesized by the following method according to the method described in J. Chem. Research(s), 1997, 250-251.

3,4-Diamino-1,2,5-thiadiazole (7.9 g, 68.2 mmol), benzyl (15.8 g, 75.0 mmol), and 230 mL of acetic acid were placed in a 500 mL three-neck flask, and agitated under refluxing for 5 hours. After naturally cooling the reaction solution to room temperature, the solvent was removed, and the product was purified by column chromatograph, thereby providing 5,6-diphenyl[1,2,5]thiadiazolo[3,4-b]pyrazine in a yield amount of 8.0 g and a yield of 41%.

Subsequently, 5,6-diphenyl[1,2,5]thiadiazolo[3,4-b]pyrazine (8.0 g, 27.7 mmol), tin(II) chloride dihydrate (31.2 g, 138.5 mmol), and 160 mL of methanol were placed in a 1,000 mL three-neck flask, to which 160 mL of concentrated sulfuric acid was slowly added, and the mixture was agitated under a nitrogen stream at 60° C. for 2 hours. The solution having been naturally cooled to room temperature was neutralized to pH 8 to 9 with a saturated sodium carbonate aqueous solution, and then methanol in the solution was distilled off to a certain extent. The precipitate was collected by filtering, and after repeating three times solid extraction with ethyl acetate, purified by column chromatography, thereby providing 2,3-diamino-5,6-diphenylpyrazine in a yield amount of 4.8 g and a yield of 66%.

(2) Synthesis Process of Intermediate B 2,3-Diamino-5,6-diphenylpyrazine (1.0 g, 3.8 mmol), 1-(4-bromophenyl)-2-phenylethan-1,2-dione synthesized by the method described in Eur. J. Org. Chem., 2012, 320-328 (1.2 g, 4.2 mmol), and 30 mL of acetic acid were placed in a 100 mL three-neck flask, and agitated under refluxing and heating for 4 hours. After naturally cooling the solution to room temperature, the solvent was distilled off, and the product was purified by column chromatography, thereby providing an intermediate B in a yield amount of 1.6 g and a yield of 88%.

(3) Synthesis Process of Example Compound (1)

The example compound (1) was synthesized by the following manner according to the manner described in Eur. J. Inorg. Chem., 2006, 3676-3683.

The intermediate B (0.39 mmol), 9,9-dimethyl-9,10-dihydroacridine synthesized by the method described in WO 2012/039561 (89 mg, 0.43 mmol), tris(dibenzylideneacetone) dipalladium(0) (36 mg, 0.039 mmol), sodium tert-butoxide (41 mg, 0.43 mmol), 20 mL of toluene, and tri(tert-butyl)phosphine (10 mg, 0.050 mmol) were placed in a 100 mL three-neck flask, and deaeration and nitrogen substitution were expeditiously repeated three times under a nitrogen stream. The mixture was agitated under a nitrogen stream under refluxing for 8 hours. After the reaction, water was added to the reaction solution having been naturally cooled to room temperature, which was then extracted with dichloromethane and rinsed with a saturated sodium chloride aqueous solution. After drying the organic layer over sodium sulfate, the solvent was distilled off, and the product was purified by column chromatography, thereby providing the example compound (1) in a yield amount of 173 mg and a yield of 69%.

Melting point: 300° C. or more $^1$H-NMR (δ ppm, CDCl$_3$) 1.69 (6H, s), 6.31 (2H, dd, J=8.4, 1.2), 6.96 (2H, td, J=7.2, 0.12), 7.33-7.48 (13H, m), 7.71 (4H, d, J=7.6), 7.77 (2H, d, J=8.0), 7.91 (2H, d, J=8.0)

Synthesis Example 2

Synthesis of Example Compound (2)

In this synthesis example, the example compound (2) was synthesized according to the following scheme.

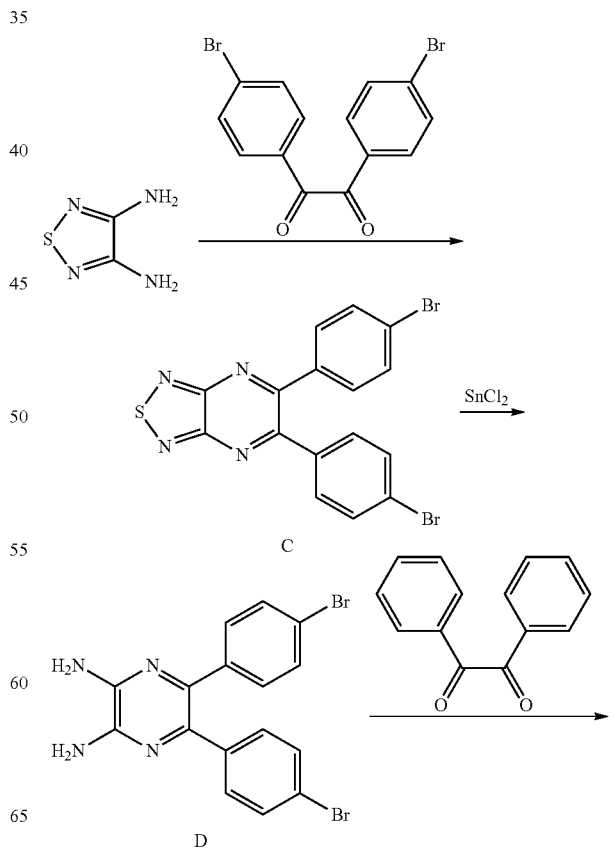

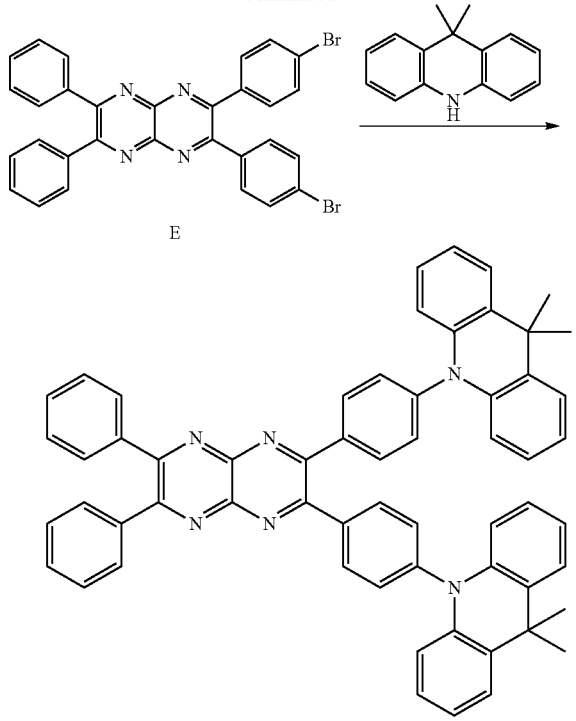

Example Compound (2)

(1) Synthesis Process of Intermediate C 3,4-Diamino-1,2,5-thiadiazole (9.9 g, 85.2 mmol), 4,4'-dibromobenzyl (24.4 g, 66.4 mmol), and 300 mL of acetic acid were placed in a 1,000 mL three-neck flask, and agitated under refluxing for 24 hours. After naturally cooling the reaction solution to room temperature, the solvent was distilled off, and the product was purified by column chromatograph, thereby providing an intermediate C in a yield amount of 19.0 g and a yield of 64%.

(2) Synthesis Process of Intermediate D

The intermediate C (21.4 g, 47.8 mmol), tin(II) chloride dihydrate (50.3 g, 222.9 mmol), and 400 mL of methanol were placed in a 1,000 mL three-neck flask, to which 400 mL of concentrated sulfuric acid was slowly added, and the mixture was agitated under a nitrogen stream at 60° C. for 3 hours. The solution having been naturally cooled to room temperature was neutralized to pH 8 to 9 with a saturated sodium carbonate aqueous solution, and then methanol in the solution was distilled off to a certain extent. The precipitate was collected by filtering, and after repeating three times solid extraction with ethyl acetate, purified by column chromatography, thereby providing an intermediate D in a yield amount of 12.0 g and a yield of 60%.

(3) Synthesis Process of Intermediate E

The intermediate D (0.6 g, 1.4 mmol), benzyl (0.33 g, 1.6 mmol), and 10 mL of acetic acid were placed in a 50 mL three-neck flask, and agitated under refluxing for 4 hours. After naturally cooling the solution to room temperature, the solvent was distilled off, and the product was purified by column chromatography, thereby providing an intermediate E in a yield amount of 0.62 g and a yield of 73%.

(4) Synthesis Process of Example Compound (2)

The same procedures as in the process (3) in Synthesis Example 1 were performed except that the intermediate E (0.39 mmol) was used instead of the intermediate B (0.39 mmol), and the amount of 9,9-dimethyl-9,10-dihydroacridine was increased twice by mol, thereby providing the example compound (2) in a yield amount of 0.24 g and a yield of 50%.

Melting point: 300° C. or more $^1$H-NMR (δ ppm, CDCl$_3$) 1.69 (12H), 6.33 (4H, m), 6.90 (8H, m), 7.37-7.53 (14H, m), 7.74 (4H, m), 8.01 (4H, d, J=8.0)

Synthesis Example 3

Synthesis of Example Compound (4)

In this synthesis example, the example compound (4) was synthesized according to the following scheme.

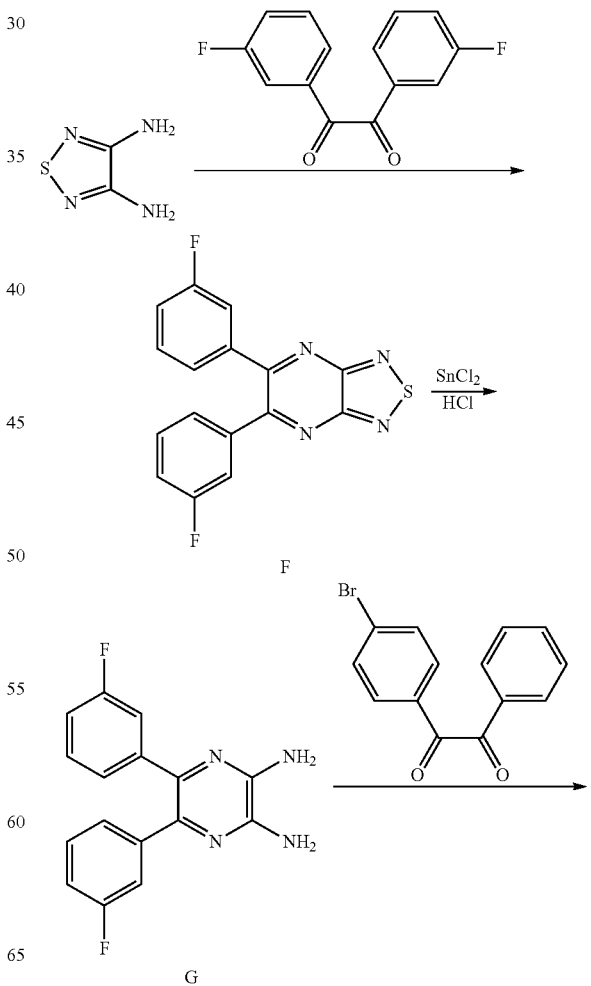

-continued

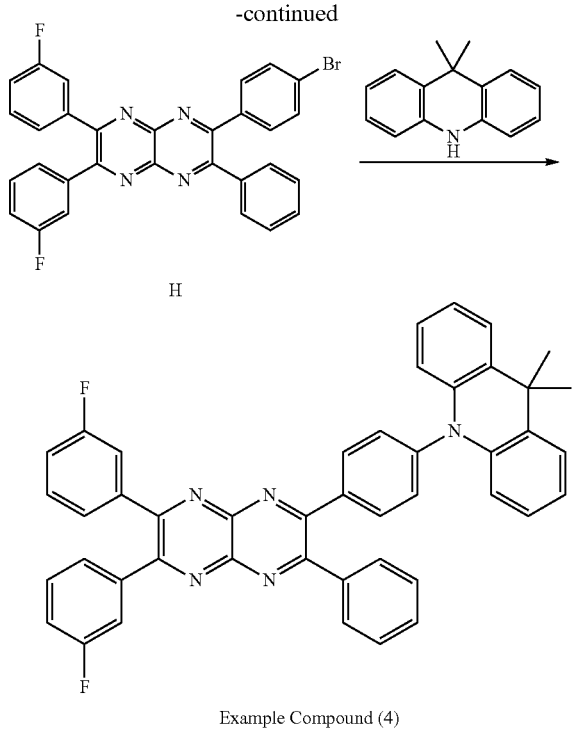

Example Compound (4)

(1) Synthesis Process of Intermediate F 3,4-Diamino-1,2,5-thiadiazole (9.9 g, 85.2 mmol), 3,3'-difluorobenzyl synthesized by the method described in Bioorgnic & Medicinal Chem., 2007, 15, 3801-3817 (16.3 g, 66.4 mmol), and 300 mL of acetic acid were placed in a 1,000 mL three-neck flask, and agitated under refluxing for 24 hours. After naturally cooling the solution to room temperature, the solvent was distilled off, and the product was purified by column chromatography, thereby providing the intermediate F in a yield amount of 18.1 g and a yield of 65%.

(2) Synthesis Process of Intermediate G

The intermediate F (15.6 g, 47.8 mmol), tin(II) chloride dihydrate (50.3 g, 222.9 mmol), and 400 mL of methanol were placed in a 1,000 mL three-neck flask, to which 400 mL of concentrated sulfuric acid was slowly added, and the mixture was agitated under a nitrogen stream at 60° C. for 3 hours. The solution having been naturally cooled to room temperature was neutralized to pH 8 to 9 with a saturated sodium carbonate aqueous solution, and then methanol in the solution was distilled off to a certain extent. The precipitate was collected by filtering, and after repeating three times solid extraction with ethyl acetate, purified by column chromatography, thereby providing an intermediate G in a yield amount of 8.6 g and a yield of 60%.

(3) Synthesis Process of Intermediate H

The intermediate G (0.60 g, 1.4 mmol), 4-bromobenzyl (0.46 g, 1.6 mmol), and 10 mL of acetic acid were placed in a 50 mL three-neck flask, and agitated under ref luxing for 4 hours. After naturally cooling the solution to room temperature, the solvent was distilled off, and the product was purified by column chromatography, thereby providing an intermediate H in a yield amount of 0.56 g and a yield of 73%.

(4) Synthesis Process of Example Compound (4)

The same procedures as in the process (3) in Synthesis Example 1 were performed except that the intermediate H (0.39 mmol) was used instead of the intermediate B (0.39 mmol), and the amount of 9,9-dimethyl-9,10-dihydroacridine was increased twice by mol, thereby providing the example compound (4) in a yield amount of 0.15 g and a yield of 55%.

Melting point: 300° C. or more

Synthesis Example 4

Synthesis of Example Compound (7)

In this synthesis example, the example compound (7) was synthesized according to the following scheme.

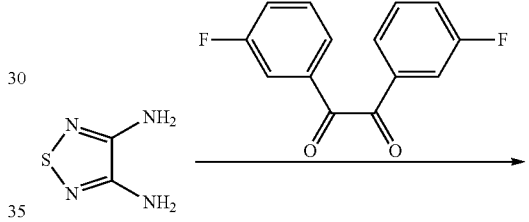

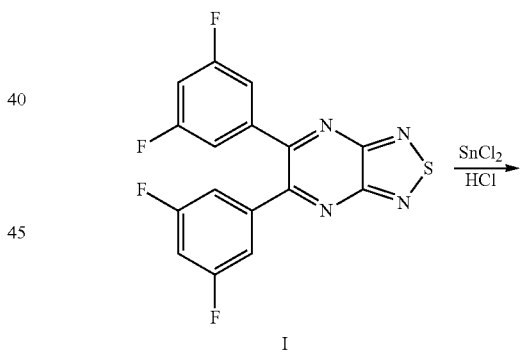

I

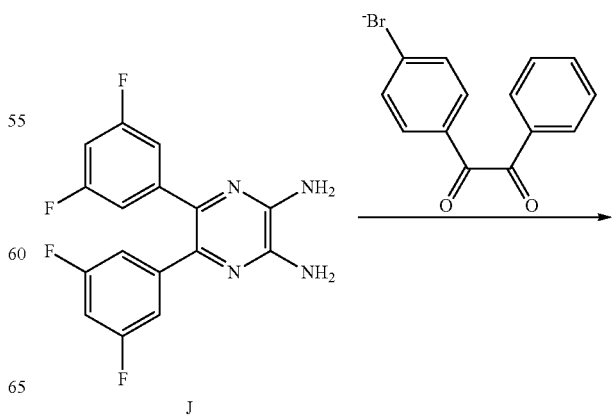

J

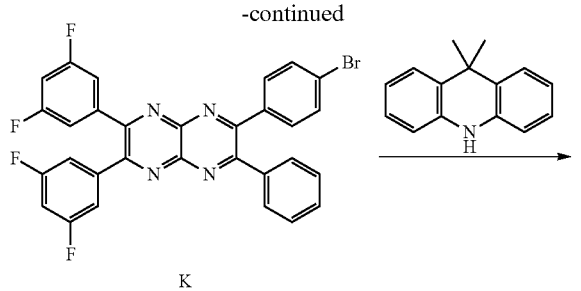

K

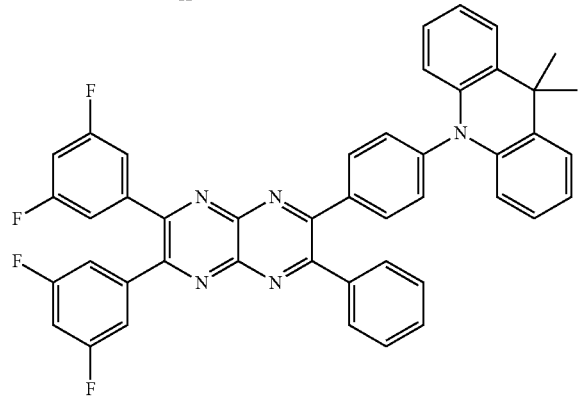

Example Compound (7)

(1) Synthesis Process of Intermediate I 3,4-Diamino-1,2,5-thiadiazole (10.0 g, 86.1 mmol), 3,3'-difluorobenzyl synthesized by the method described in Bioorgnic & Medicinal Chem., 2007, 15, 3801-3817 (16.5 g, 67.2 mmol), and 300 mL of acetic acid were placed in a 1,000 mL three-neck flask, and agitated under refluxing for 24 hours. After naturally cooling the solution to room temperature, the solvent was distilled off, and the product was purified by column chromatography, thereby providing the intermediate I in a yield amount of 14.6 g and a yield of 65%.

(2) Synthesis Process of Intermediate J

The intermediate I (21.4 g, 47.8 mmol), tin(II) chloride dihydrate (50.3 g, 222.9 mmol), and 400 mL of methanol were placed in a 1,000 mL three-neck flask, to which 400 mL of concentrated sulfuric acid was slowly added, and the mixture was agitated under a nitrogen stream at 60° C. for 3 hours. The solution having been naturally cooled to room temperature was neutralized to pH 8 to 9 with a saturated sodium carbonate aqueous solution, and then methanol in the solution was distilled off to a certain extent. The precipitate was collected by filtering, and after repeating three times solid extraction with ethyl acetate, purified by column chromatography, thereby providing an intermediate J in a yield amount of 9.6 g and a yield of 60%.

(3) Synthesis Process of Intermediate K

The intermediate J (0.6 g, 1.8 mmol), 4-bromobenzyl (0.58 g, 2.0 mmol), and 10 mL of acetic acid were placed in a 50 mL three-neck flask, and agitated under refluxing for 4 hours. After naturally cooling the solution to room temperature, the solvent was distilled off, and the product was purified by column chromatography, thereby providing an intermediate K in a yield amount of 0.78 g and a yield of 73%.

(4) Synthesis Process of Example Compound (7)

The same procedures as in the process (3) in Synthesis Example 1 were performed except that the intermediate K (0.39 mmol) was used instead of the intermediate B (0.39 mmol), thereby providing the example compound (7) in a yield amount of 0.14 g and a yield of 50%.

Melting point: 300° C. or more

Synthesis Example 5

Synthesis of Example Compound (11)

The intermediate B synthesized in Synthesis Example 1 (0.2 g, 0.39 mmol), phenoxazine (78 mg, 0.43 mmol), palladium(II) acetate (5 mg, 0.023 mmol), potassium carbonate (0.16 g, 1.16 mmol), 20 mL of toluene, and tri(tert-butyl)phosphine (17 mg, 0.085 mmol) were placed in a 100 mL three-neck flask, and deaeration and nitrogen substitution were expeditiously repeated three times under agitation. The mixture was agitated under a nitrogen stream under refluxing for 10 hours. After the reaction, water was added to the reaction solution having been naturally cooled to room temperature, which was then extracted with dichloromethane and rinsed with a saturated sodium chloride aqueous solution. After drying the organic layer over sodium sulfate, the solvent was distilled off, and the product was purified by column chromatography, thereby providing the example compound (11) in a yield amount of 0.14 g and a yield of 59%.

Melting point: 300° C. or more $^1$H-NMR (δ ppm, CDCl$_3$) 5.96 (2H, dd, J=8.0, 1.6), 6.60-6.78 (6H, m), 7.33-7.53 (12H, m), 7.67-7.80 (6H, m), 7.87 (2H, d, J=8.0)

Synthesis Example 6

Synthesis of Example Compound (12)

The intermediate E synthesized in Synthesis Example 2 (0.2 g, 0.34 mmol), phenoxazine (0.14 g, 0.74 mmol), palladium(II) acetate (5 mg, 0.020 mmol), potassium carbonate (0.28 g, 2.02 mmol), 20 mL of toluene, and tri(tert-butyl)phosphine (15 mg, 0.074 mmol) were placed in a 100 mL three-neck flask, and deaeration and nitrogen substitution were expeditiously repeated three times under a nitrogen stream. The mixture was agitated under a nitrogen stream under refluxing for 9 hours. After the reaction, water was added to the reaction solution having been naturally cooled to room temperature, which was then extracted with dichloromethane and rinsed with a saturated sodium chloride aqueous solution. After drying the organic layer over sodium sulfate, the solvent was distilled off, and the product was purified by column chromatography, thereby providing the example compound (12) in a yield amount of 0.19 g and a yield of 71%.

Melting point: 300° C. or more $^1$H-NMR (δ ppm, CDCl$_3$) 5.96 (4H, dd, J=8.0, 1.6), 6.53 (4H, td, J=8.0, 1.6), 6.66 (4H, td, J=8.0, 1.6), 6.71 (4H, dd, J=8.0, 1.6), 7.37-7.48 (10H, m), 7.72 (4H, d, J=7.2), 7.95 (4H, d, J=8.8)

Synthesis Example 7

Synthesis of Example Compound (25)

In this synthesis example, the example compound (25) was synthesized according to the following scheme.

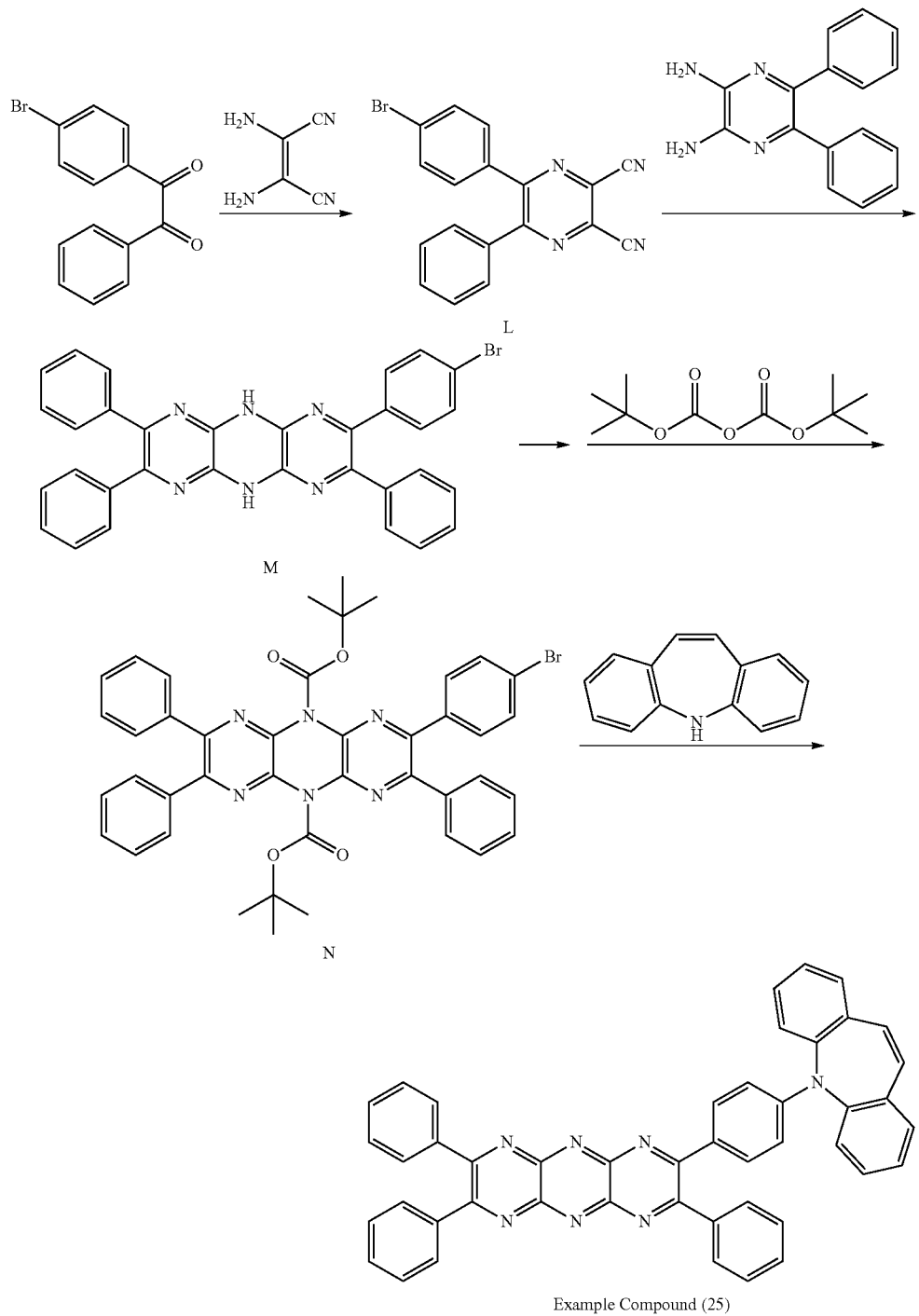

Example Compound (25)

(1) Synthesis Process of Intermediate L

4-Bromobenzyl (7.9 g, 27.2 mmol), diaminomaleonitrile (3.5 g, 32.6 mmol), and 120 mL of acetic acid were placed in a 500 mL three-neck flask, and agitated under refluxing for 4 hours. After completing the reaction, the reaction solution was naturally cooled, and after distilling of f the solvent, the product was purified by column chromatography, thereby providing the intermediate L in a yield amount of 9.8 g and a yield of 93%.

(2) Synthesis Process of Intermediate M

The intermediate L (1.9 g, 5.2 mmol), 2,3-diamino-5,6-diphenylpyrazine (1.0 g, 5.8 mmol), potassium carbonate (1.3 g, 9.5 mmol), and 30 mL of dimethylsulfoxide were placed in a 100 mL three-neck flask, and deaeration and nitrogen substitution were repeated three times. The mixed solution was agitated under a nitrogen stream at 120° C. for 7 hours. The reaction solution was naturally cooled, and the extracted with dichloromethane and distilled water. The organic layer and a sodium dithionite aqueous solution were placed in a separating funnel and separated, and after drying the organic layer over sodium sulfate, the product was purified by column chromatography, thereby providing an intermediate M in a yield amount of 0.89 g and a yield of 30%.

(3) Synthesis Process of Intermediate N

The intermediate M (0.63 g, 1.1 mmol), di-tert-butyl dicarbonate (0.52 g, 2.4 mmol), triethylamine (0.24 g, 2.37 mmol), N,N-dimethyl-4-aminopyridine (26 mg, 0.22 mmol), and 30 mL of tetrahydrofuran were placed in a 100 mL flask, and agitated at room temperature for 7 hours. After the reaction, the solvent was distilled off from the reaction solution, approximately from 20 to 30 mL of ethyl acetate was added to the resulting residue, and the mixture was filtered to remove impurities to the filtrate. The resulting residue was purified by column chromatography, thereby providing an intermediate N in a yield amount of 0.56 g and a yield of 66%.

(4) Synthesis Process of Example Compound (25)

The intermediate N (0.31 g, 0.40 mmol), iminostilbene (0.12 g, 0.60 mmol), tris(dibenzylideneacetone) dipalladium (0) (36 mg, 0.040 mmol), sodium tert-butoxide (0.57 g, 5.96 mmol), 20 mL of toluene, and tri(tert-butyl)phosphine (10 mg, 0.052 mmol) were placed in a 100 mL three-neck flask, and deaeration and nitrogen substitution were expeditiously repeated three times under a nitrogen stream. The mixture was agitated under a nitrogen stream under refluxing for 26 hours. After the reaction, water was added to the reaction solution having been naturally cooled to room temperature, which was then extracted with dichloromethane and rinsed with a saturated sodium chloride aqueous solution. After drying the organic layer over sodium sulfate, the solvent was distilled off, and the product was purified by column chromatography, thereby providing the example compound (25) in a yield amount of 0.13 g and a yield of 46%.

Melting point: 300° C. or more

Example 1

Production and Evaluation of Solution of Example Compound (1)

A toluene solution (concentration: $10^{-5}$ M) of the example compound (1) produced in Synthesis Example 1 was prepared.

The toluene solution was measured for a photoluminescence quantum efficiency with excitation light of 380 nm, the photoluminescence quantum efficiency was 12.5% for the toluene solution without nitrogen bubbling, and 33.4% for the toluene solution with nitrogen bubbling.

Figure 2:
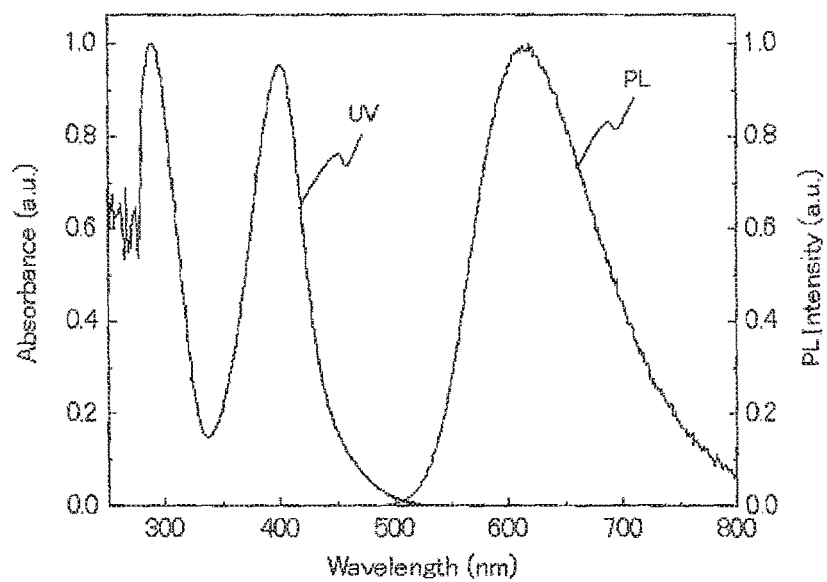
FIG. 2 is the light emission and absorption spectra of the toluene solution of the example compound (1) in Example 1.

FIG. 2 shows the results of the measurement of the photoluminescence spectrum and the ultraviolet ray absorption spectrum with excitation light of 400 nm for the toluene solution. The maximum light emission wavelength λmax was 651 nm.

Figure 3:
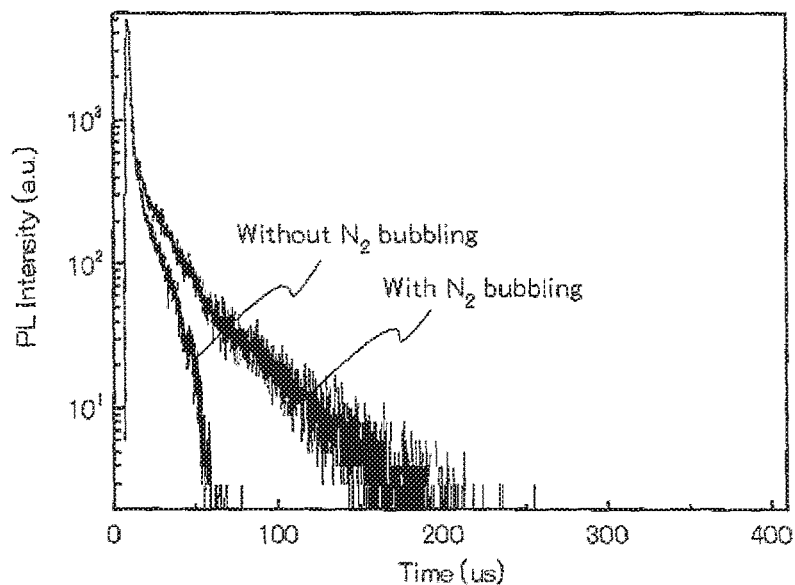
FIG. 3 is the transient decay curves of the toluene solution of the example compound (1) in Example 1.

FIG. 3 shows the results of the measurement of the transient decay curves with excitation light of 340 nm. The transient decay curve shows the measurement result of the light emission lifetime obtained by measuring the process where the light emission intensity is deactivated on irradiating the compound with excitation light. In ordinary one-component light emission (fluorescent light or phosphorescent light), the light emission intensity is decays monoexponentially. This means that the light emission intensity decays linearly on a graph with the semilogarithm as the ordinate. In a transient decay curve of the example compound (1) shown in FIG. 3, while a linear component (fluorescent light) was observed in the initial stage of observation, a component that deviated from the linearity appeared after several microseconds. The later component is light emission of the delayed component, and the signal thereof added to the initial component appears as a long tail curve on the longer time side. Thus, the measurement of the light emission lifetime revealed that the example compound (1) was a light-emitting material that contained a delayed component in addition to a fluorescent component.

The light emission lifetime was 0.37 μs for the toluene solution without nitrogen bubbling, and 36.1 μs for the toluene solution with nitrogen bubbling.

The energy difference $\Delta E_{st}$ between the excited singlet state and the excited triplet state of the toluene solution was 0.002 eV, and the f value as the frequency factor of the $S_0$-$S_1$ transition was 0.0002. The $\Delta E_{st}$ value was used as a scale of the probability of the thermal activation, and it was understood that a smaller value thereof provided a large possibility of occurrence of thermal activation type delayed fluorescence. The f value meant the probability of occurrence of the transition from $S_0$ (ground state) to $S_1$ (excited singlet state), and was used as a scale of the probability of the light emission (fluorescent light intensity) in this calculation, and it was understood that a larger value thereof provided a possibility of more intense fluorescent light.

Example 2

Production and Evaluation of Solution of Example Compound (2)

A toluene solution (concentration: $10^{-5}$ M) of the example compound (2) produced in Synthesis Example 2 was prepared.

The toluene solution was measured for a photoluminescence quantum efficiency with excitation light of 440 nm, the photoluminescence quantum efficiency was 12.0% for the toluene solution without nitrogen bubbling, and 32.4% for the toluene solution with nitrogen bubbling.

Figure 4:
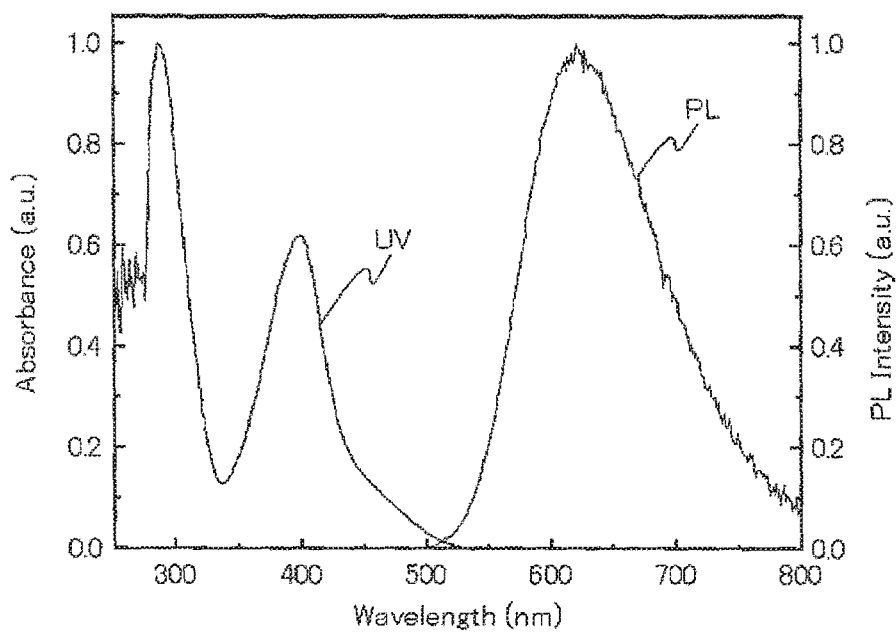
FIG. 4 is the light emission and absorption spectra of the toluene solution of the example compound (2) in Example 2.
Figure 5:
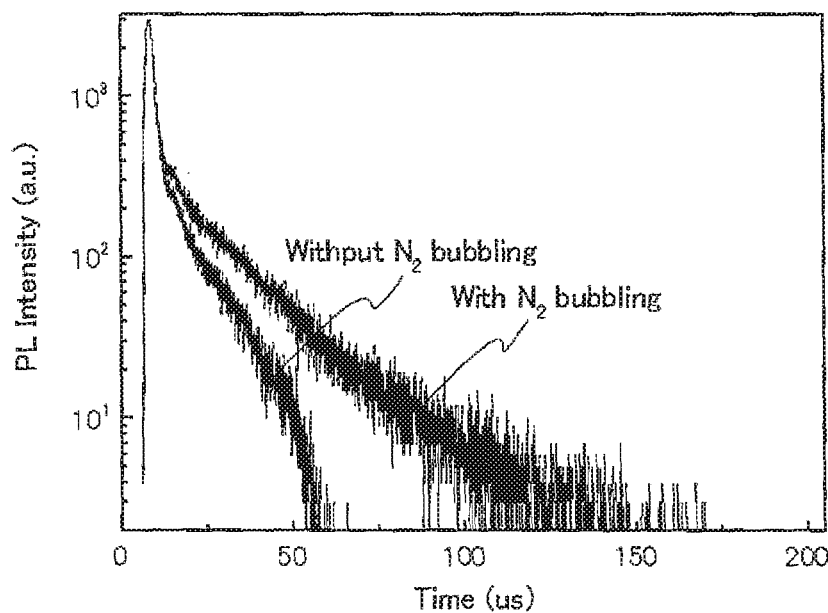
FIG. 5 is the transient decay curves of the toluene solution of the example compound (2) in Example 2.

FIG. 4 shows the results of the measurement of the photoluminescence spectrum and the ultraviolet ray absorption spectrum with excitation light of 444 nm for the toluene solution, and FIG. 5 shows the results of the measurement of the transient decay curves with excitation light of 340 nm. FIG. 4 showed that the maximum light emission wavelength λmax was 621 nm. FIG. 5 showed a component with a short light emission lifetime (i.e., a prompt fluorescent component) and a component with a long light emission lifetime (i.e., a delayed fluorescent component) observed, and the light emission lifetime of the delayed fluorescent component was 0.40 μs for the toluene solution without nitrogen bubbling, and 23.5 μs for the toluene solution with nitrogen bubbling. The toluene solution exhibited an energy difference $\Delta E_{st}$ between the excited singlet state and the excited triplet state of 0.002 eV and an f value of 0.

Comparative Example 1

Production and Evaluation of Solution of Comparative Compound (A)

A toluene solution (concentration: $10^{-5}$ M) of the comparative compound (A) was prepared.

The evaluation of the characteristics of the toluene solution revealed that the photoluminescence quantum efficiency with excitation light of 320 nm was 1.2% for the toluene solution without nitrogen bubbling, and 2.3% for the toluene solution with nitrogen bubbling, and the maximum light emission wavelength was 706 nm. The energy difference $\Delta E_{st}$ between the excited singlet state and the excited triplet state was 0.047 eV and, and the f value was 0.031. The toluene solution of the comparative compound (A) showed weak light emission, and no delayed fluorescence was observed.

Comparative Compound (A)

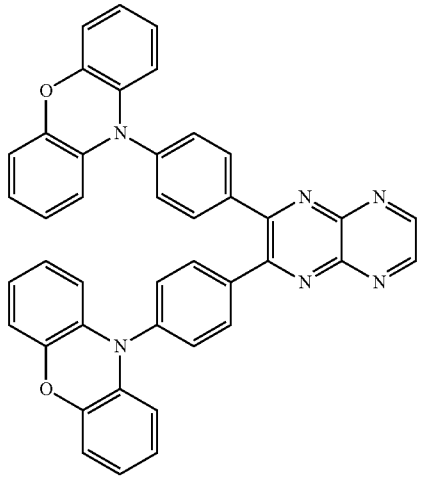

Comparative Example 2

Production and Evaluation of Solution of Comparative Compound (B)

A toluene solution (concentration: $10^{-5}$ M) of the comparative compound (B) was prepared.

The evaluation of the characteristics of the toluene solution revealed that the photoluminescence quantum efficiency with excitation light of 360 nm was 1.1% for the toluene solution without nitrogen bubbling, and 2.3% for the toluene solution with nitrogen bubbling, and the maximum light emission wavelength was 697 nm. The energy difference $\Delta E_{st}$ between the excited singlet state and the excited triplet state was 0.006 eV and, and the f value was 0.041. The toluene solution of the comparative compound (B) showed weak light emission, and no delayed fluorescence was observed.

Comparative Compound (B)

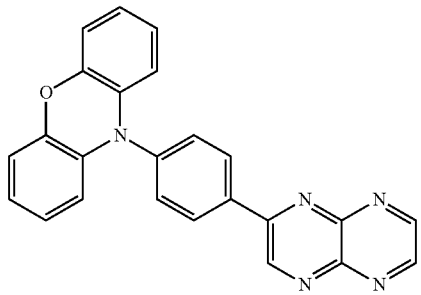

Comparative Example 3

Production and Evaluation of Solution of Comparative Compound (C)

A toluene solution (concentration: $10^{-5}$ M) of the comparative compound (C) was prepared.

The toluene solution was observed for photoluminescence with excitation light of 360 nm, but no delayed fluorescence was clearly observed.

Comparative Compound (C)

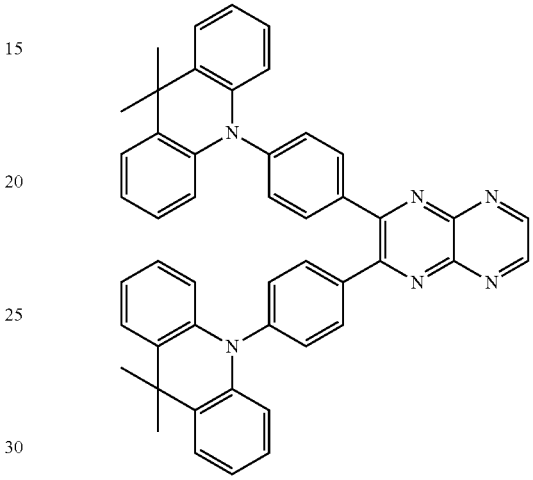

Example 3

Production and Evaluation of Thin Film Organic Photoluminescent Device of Example Compound (2)

On a silicon substrate, the example compound (2) and mCBP were vapor-deposited from separate vapor deposition sources under a condition of a vacuum degree of $3.0 \times 10^{-4}$ Pa or less to form a thin film having a concentration of the example compound (2) of 6.0% by weight to a thickness of 50 nm, thereby providing a thin film organic photoluminescent device.

Figure 6:
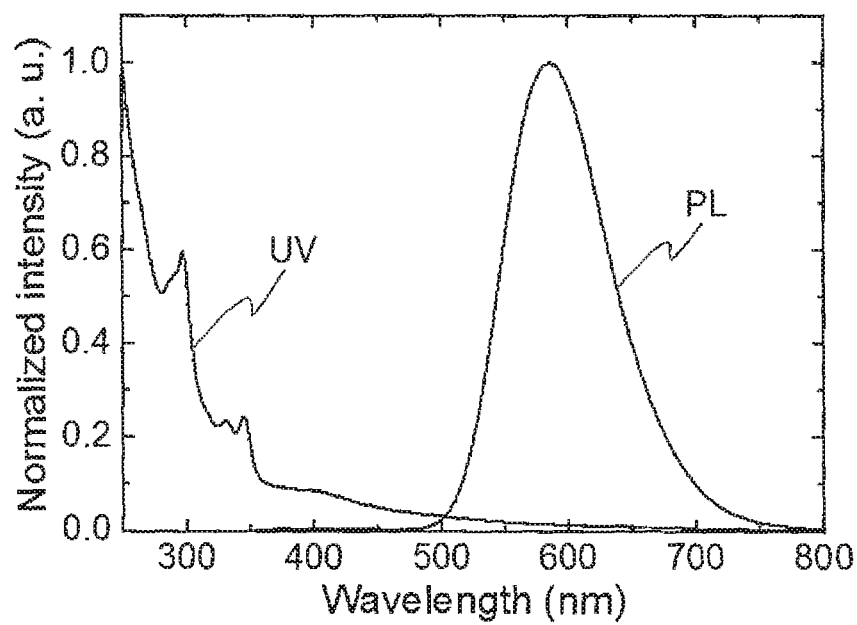
FIG. 6 is the light emission and absorption spectra of the organic photoluminescent device of the example compound (2) in Example 3.
Figure 7:
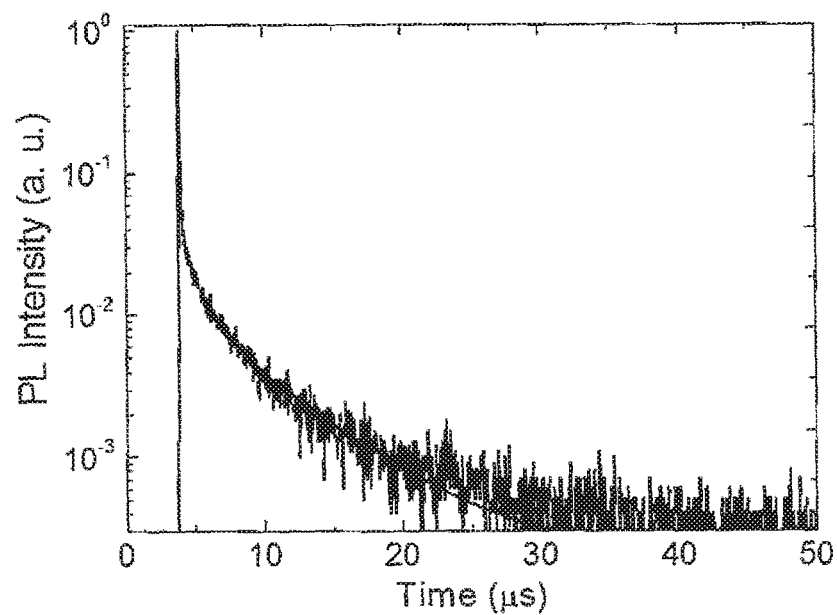
FIG. 7 is the transient decay curve of the organic photoluminescent device of the example compound (2) in Example 3.

FIG. 6 shows the results of the measurement of the photoluminescence spectrum and the ultraviolet ray absorption spectrum with excitation light of 400 nm for the thin film organic photoluminescent device, and FIG. 7 shows the results of the measurement of the transient decay curve thereof measured in the air atmosphere. The photoluminescence quantum efficiency was 48.9% in the air, and 50.1% in a nitrogen-containing atmosphere, and the light emission wavelength was 586 nm. FIG. 7 showed three components having light emission lifetimes different from each other, and the light emission lifetimes of the components were 7.81 ns, 969.0 ns, and 5.73 µs.

Example 4

Production and Evaluation of Organic Electroluminescent Device of Example Compound (2)

Thin films were laminated on a glass substrate having formed thereon an anode formed of indium tin oxide (ITO) having a thickness of 100 nm, by a vacuum vapor deposition method at a vacuum degree of $3.0 \times 10^{-4}$ Pa. Firstly, α-NPD was formed to a thickness of 35 nm on ITO, and then the example compound (2) and mCBP were co-deposited thereon from separate vapor deposition sources to form a layer having a thickness of 15 nm, which was designated as a light-emitting layer. At this time, the concentration of the example compound (2) was 6.0% by weight. TPBi was then formed to a thickness of 65 nm, further lithium fluoride (LiF) was vacuum vapor-deposited to a thickness of 0.8 nm, and then aluminum (Al) was vapor-deposited to a thickness of 100 nm to form a cathode, thereby completing an organic electroluminescent device.

Figure 8:
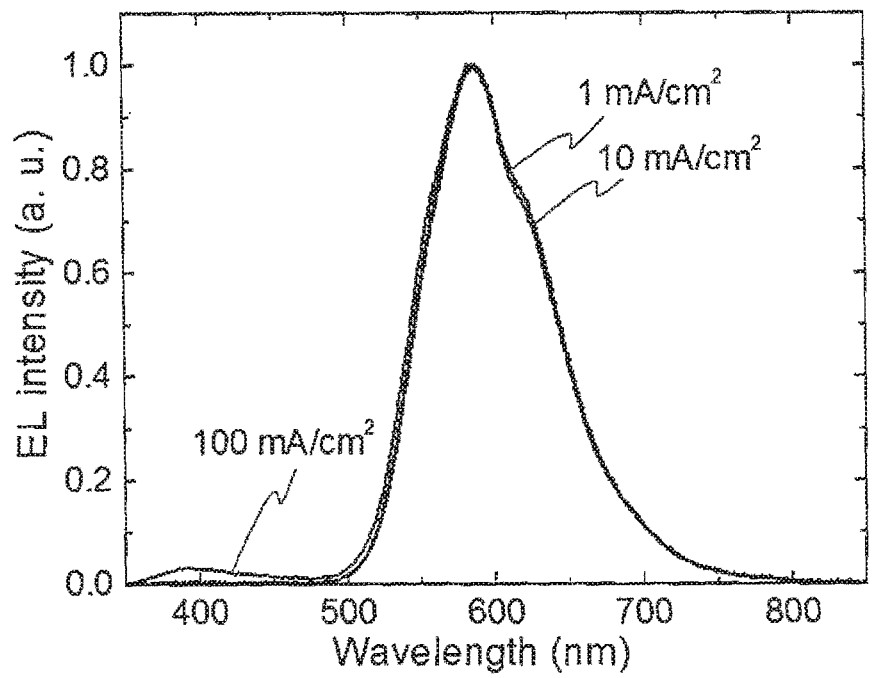
FIG. 8 is the light emission spectra of the organic electroluminescent device of the example compound (2) in Example 4.
Figure 9:
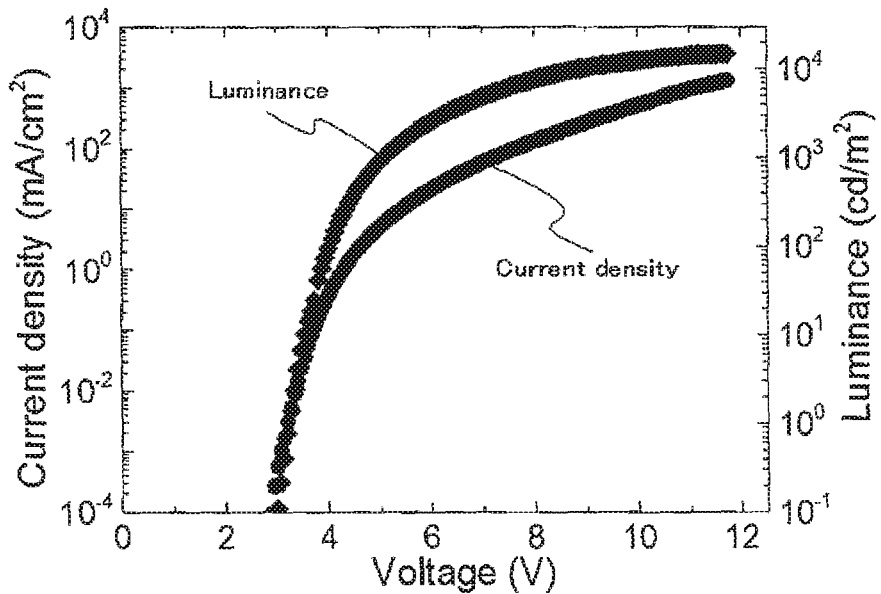
FIG. 9 is a graph showing the voltage-current density-luminance characteristics of the organic electroluminescent device of the example compound (2) in Example 4.
Figure 10:
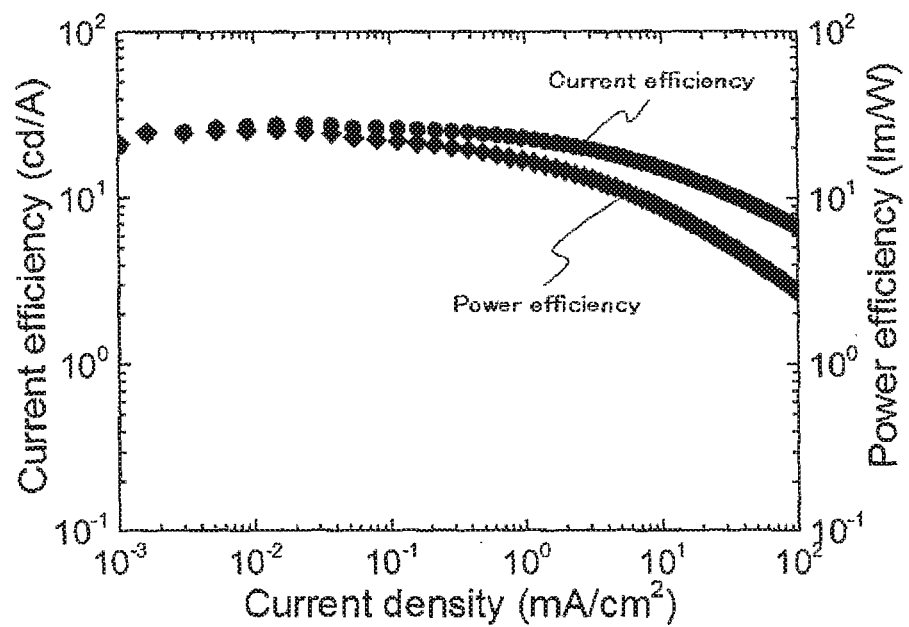
FIG. 10 is a graph showing the current density-current efficiency-power efficiency characteristics of the organic electroluminescent device of the example compound (2) in Example 4.
Figure 11:
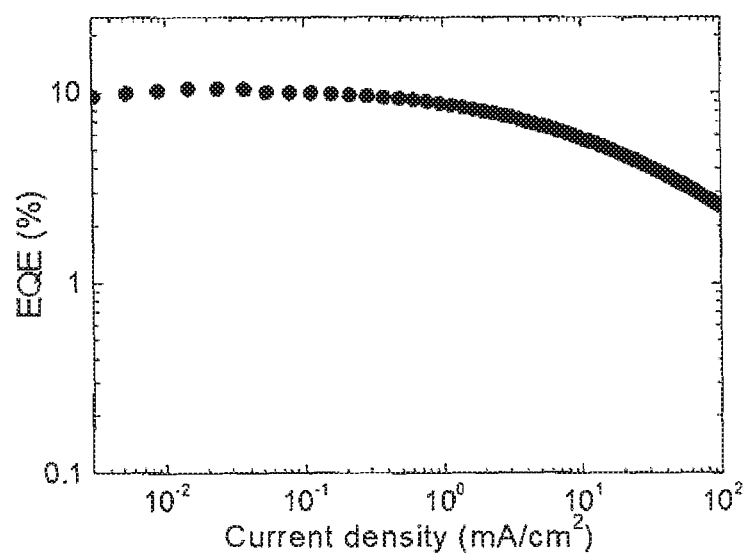
FIG. 11 is a graph showing the current density-external quantum efficiency characteristics of the organic electroluminescent device of the example compound (2) in Example 4.

FIG. 8 shows the light emission spectra of the organic electroluminescent device thus produced, measured under conditions of 1 mA/cm², 10 mA/cm², and 100 mA/cm², FIG. 9 shows the voltage-current density-luminance characteristics thereof, FIG. 10 shows the current density-current efficiency-power efficiency characteristics thereof, and FIG. 11 shows the current density-external quantum efficiency characteristics thereof. The organic electroluminescent device exhibited a turn-on voltage of 3.2 V, a maximum luminance of 14,820 cd/m², a maximum current efficiency of 27.7 cd/A, and a maximum power efficiency of 25.1 lm/W. The organic electroluminescent device achieved a high external quantum efficiency of 10.5%. If an ideally balanced organic electroluminescent device is produced by using a fluorescent material having a light emission quantum efficiency of 100%, the external quantum efficiency of the fluorescent light emission may be from 5 to 7.5% assuming that the light extraction efficiency is from 20 to 30%. It has been ordinarily considered that this value is the theoretical limit value of an external quantum efficiency of an organic electroluminescent device using a fluorescent material. The organic electroluminescent device of the invention is considerably excellent in such a point that a high external quantum efficiency that exceeds the theoretical limit value is achieved.

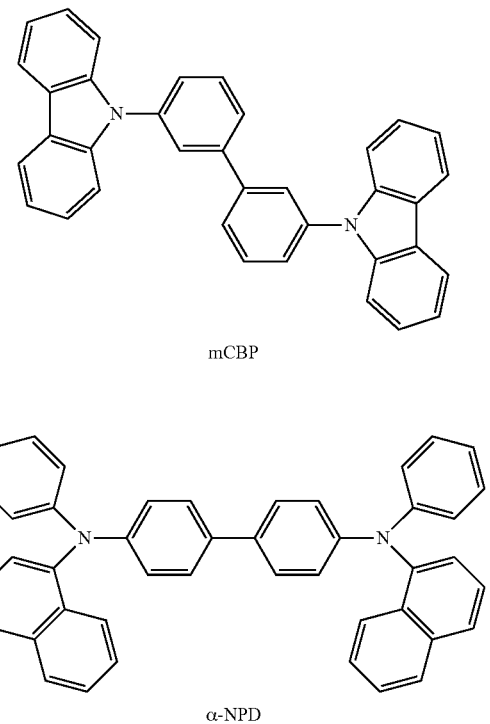

mCBP

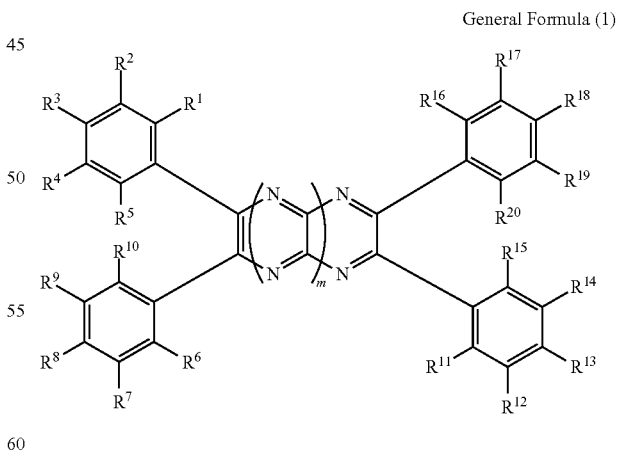

α-NPD

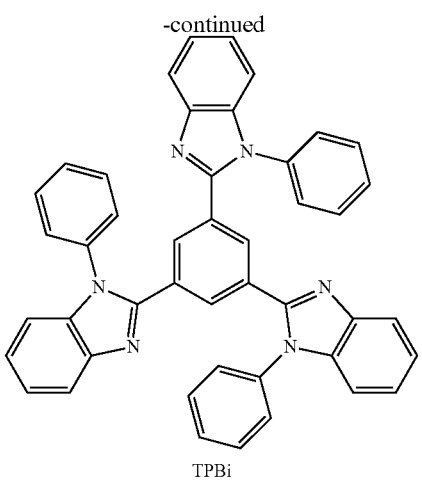

TPBi

INDUSTRIAL APPLICABILITY

The organic light-emitting device of the invention is capable of achieving a high light emission efficiency. The compound of the invention is useful as a light-emitting material for the organic light-emitting device. Accordingly the invention has high industrial applicability.

REFERENCE SIGNS LIST

1 substrate
2 anode
3 hole injection layer
4 hole transporting layer
5 light-emitting layer
6 electron transporting layer
7 cathode

The invention claimed is:
1. A light-emitting material comprising a compound represented by the following general formula (1):

General Formula (1)

wherein in the general formula (1), $R^1$ to $R^5$ each independently represent a hydrogen atom or a substituent having a Hammett $\sigma_p$ value of 0 or more; $R^6$ to $R^{20}$ each independently represent a hydrogen atom or a substituent, provided that at least one of $R^6$ to $R^{20}$ represents a substituted or unsubstituted N, N-diarylamino group; and m represents 1 or 2.

2. The light-emitting material according to claim 1, wherein the substituent having a Hammett $\sigma_p$ value of 0 or more is a halogen atom, an acyloxy group, an alkoxycarbonyl group, an aryloxycarbonyl group, a phenyl group, or a cyano group.

3. The light-emitting material according to claim 1, wherein the substituted or unsubstituted N,N-diarylamino group is a group represented by the following general formula (2):

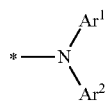

General Formula (2)

wherein in the general formula (2), $Ar^1$ and $Ar^2$ each independently represent a substituted or unsubstituted aromatic group having from 6 to 10 carbon atoms; and * represents a bonding position, provided that in the case where the compound represented by the general formula (1) has plural groups each represented by the general formula (2), the groups represented by $Ar^1$ may be the same as or different from each other, and the groups represented by $Ar^2$ may be the same as or different from each other.

4. The light-emitting material according to claim 3, wherein $Ar^1$ and $Ar^2$ are bonded directly or indirectly to each other to form a ring.

5. The light-emitting material according to claim 4, wherein the group represented by the general formula (2) is represented by the following general formula (3):

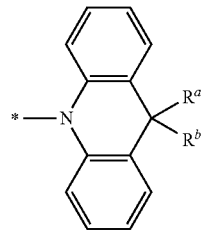

General Formula (3)

wherein in the general formula (3), $R^a$ and $R^b$ each independently represent a hydrogen atom, a substituted or unsubstituted alkyl group having from 1 to 5 carbon atoms, or a substituted or unsubstituted aromatic group having from 6 to 10 carbon atoms; and * represents a bonding position, provided that in the case where the compound represented by the general formula (1) has plural groups each represented by the general formula (3), the groups represented by Ra may be the same as or different from each other, and the groups represented by Rb may be the same as or different from each other.

6. The light-emitting material according to claim 1, wherein in the general formula (1), m is 1.

7. The light-emitting material according to claim 1, wherein the light-emitting material emits delayed fluorescent light.

8. A compound represented by the following general formula (11):

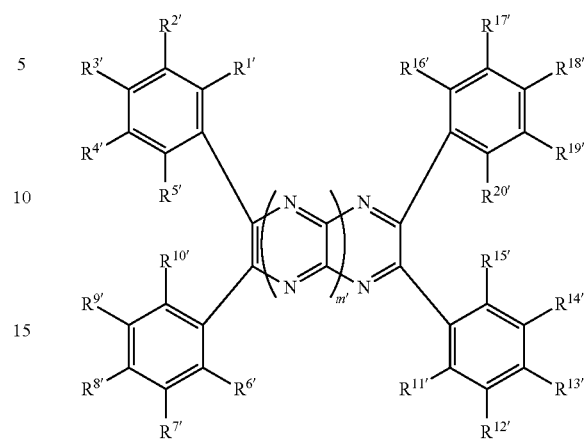

General Formula (11)

wherein in the general formula (11), $R^{1'}$ to $R^{5'}$ each independently represent a hydrogen atom or a substituent having a Hammett $\sigma_p$ value of 0 or more; $R^{6'}$ to $R^{20'}$ each independently represent a hydrogen atom or a substituent, provided that at least one of $R^{6'}$ to $R^{20'}$ represents a substituted or unsubstituted N,N-diarylamino group; and m' represents 1 or 2.

9. The compound according to claim 8, wherein the compound represented by the general formula (11) is represented by the following general formula (12):

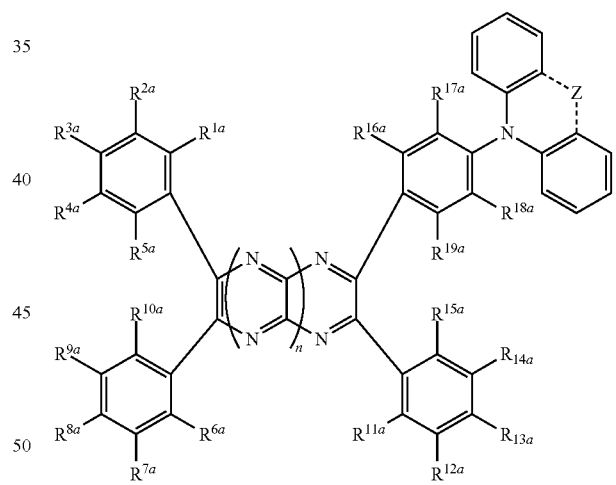

General Formula (12)

wherein in the general formula (12), $R^{1a}$ to $R^{5a}$ and $R^{16a}$ to $R^{19a}$ each independently represent a hydrogen atom or a substituent having a Hammett $\sigma_p$ value of 0 or more; $R^{6a}$ to $R^{15a}$ each independently represent a hydrogen atom, a substituent having a Hammett $\sigma_p$ value of 0 or more, or a substituted or unsubstituted N,N-diarylamino group; n represents 1 or 2; and Z represents a linking group containing a carbon chain for forming a 6-membered or 7-membered ring, or an oxygen atom for forming a 6-membered ring.

10. The compound according to claim 9, wherein $R^{1a}$ to $R^{5a}$ each independently represent a hydrogen atom or a fluorine atom.

11. An organic light-emitting device comprising a substrate having thereon a light-emitting layer containing the light-emitting material according to claim 1.

12. The organic light-emitting device according to claim 11, wherein the light-emitting device emits delayed fluorescent light.

13. The organic light-emitting device according to claim 11, wherein the light-emitting device is an organic electroluminescent device.

* * * * *